(12) United States Patent
Kelley et al.

(10) Patent No.: US 10,888,864 B2
(45) Date of Patent: Jan. 12, 2021

(54) ELECTROCHEMICAL METABOLIC ACTIVITY DETECTING DEVICE

(71) Applicant: The Governing Council of the University of Toronto, Toronto (CA)

(72) Inventors: Shana Olwyn Kelley, Toronto (CA); Edward Hartley Sargent, Toronto (CA); Justin David Besant, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 16/570,267

(22) Filed: Sep. 13, 2019

(65) Prior Publication Data

US 2020/0030803 A1 Jan. 30, 2020

Related U.S. Application Data

(63) Continuation of application No. 15/523,131, filed as application No. PCT/CA2015/051102 on Oct. 28, 2015, now Pat. No. 10,449,542.

(Continued)

(51) Int. Cl.
*B01L 3/00* (2006.01)
*G01N 33/49* (2006.01)
(Continued)

(52) U.S. Cl.
CPC ......... *B01L 3/502761* (2013.01); *C12Q 1/02* (2013.01); *G01N 1/40* (2013.01);
(Continued)

(58) Field of Classification Search
CPC ....... B01L 3/502761; B01L 3/00; C12Q 1/02; G01N 1/40; G01N 33/48735; G01N 33/49;
(Continued)

(56) References Cited

U.S. PATENT DOCUMENTS

2003/0070677 A1* 4/2003 Handique ............ B01F 5/0085
128/203.12
2010/0003666 A1* 1/2010 Lee ...................... C12Q 1/6816
435/5
(Continued)

FOREIGN PATENT DOCUMENTS

WO 2004/065618 A2 8/2004
WO 2006/050972 A1 5/2006
(Continued)

OTHER PUBLICATIONS

Athina Nickitas-Etienne—International Bureau of WIPO, "International Preliminary Report on Patentability", for International Application No. PCT/CA2015/051102 dated May 2, 2017.

*Primary Examiner* — Brian J. Sines

(57) ABSTRACT

Methods and devices for detecting metabolic activity of target cells in a sample. The target cells are concentrated in a nanoliter well having a microfilter. A reporter compound that exhibits a change in electrochemical state in response to metabolic activity of the target cells is introduced. Metabolic activity or viability of the target cells is detected based on a determined change in the electrochemical state of contents in the well.

10 Claims, 39 Drawing Sheets

Related U.S. Application Data

(60) Provisional application No. 62/069,601, filed on Oct. 28, 2014.

(51) Int. Cl.
*G01N 35/00* (2006.01)
*G01N 33/48* (2006.01)
*G01N 1/40* (2006.01)
*C12Q 1/02* (2006.01)
*G01N 33/50* (2006.01)
*G01N 33/487* (2006.01)
*G01N 33/493* (2006.01)

(52) U.S. Cl.
CPC ....... *G01N 33/48735* (2013.01); *G01N 33/49* (2013.01); *G01N 33/493* (2013.01); *G01N 33/5005* (2013.01); *B01L 2200/0668* (2013.01); *B01L 2200/0673* (2013.01); *B01L 2300/0645* (2013.01); *B01L 2300/0681* (2013.01); *B01L 2300/0816* (2013.01); *B01L 2300/0864* (2013.01); *B01L 2400/0487* (2013.01); *B01L 2400/0633* (2013.01)

(58) Field of Classification Search
CPC .. G01N 33/493; G01N 33/5005; G01N 35/00; G01N 33/48; G01N 15/06; G01N 33/00
See application file for complete search history.

(56) References Cited

U.S. PATENT DOCUMENTS

| | | | |
|---|---|---|---|
| 2010/0022416 A1* | 1/2010 | Flemming | B01L 3/5085 506/39 |
| 2016/0061811 A1* | 3/2016 | Kelley | G01N 33/54326 73/61.72 |
| 2016/0146823 A1* | 5/2016 | Chiu | G01N 33/5304 506/9 |
| 2018/0326417 A1* | 11/2018 | Wikswo | B01L 3/502707 |
| 2019/0046984 A1* | 2/2019 | Kelley | B01L 3/502761 |

FOREIGN PATENT DOCUMENTS

WO 2012/109157 A2 8/2012
WO 2014/166000 A1 10/2014

\* cited by examiner

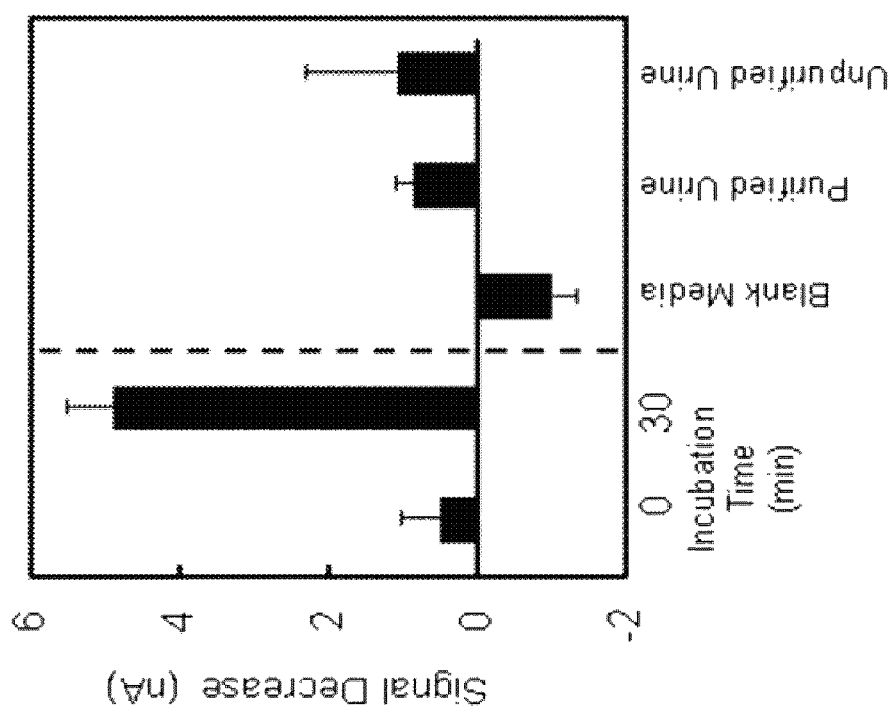

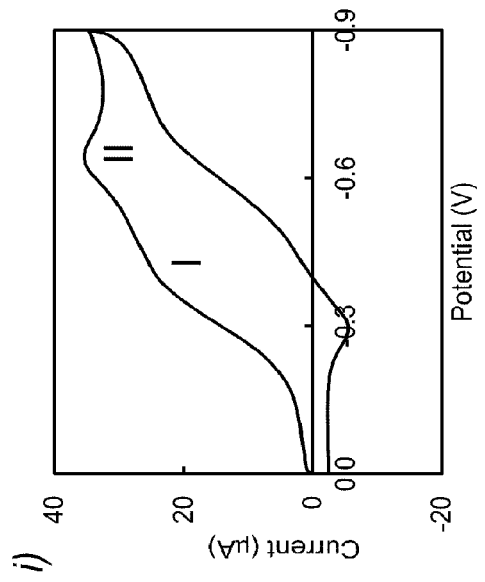
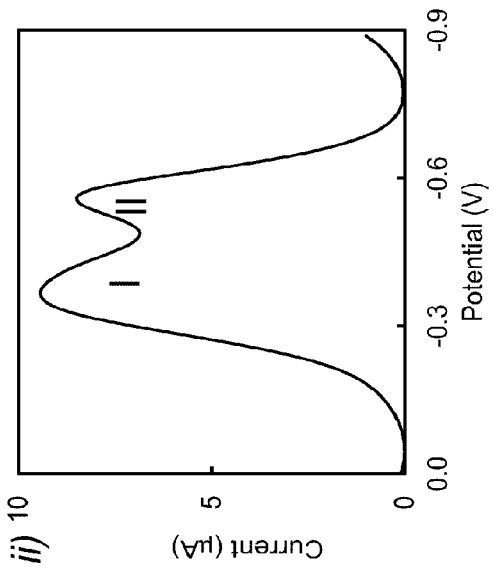
FIG 6A
FIG 6B
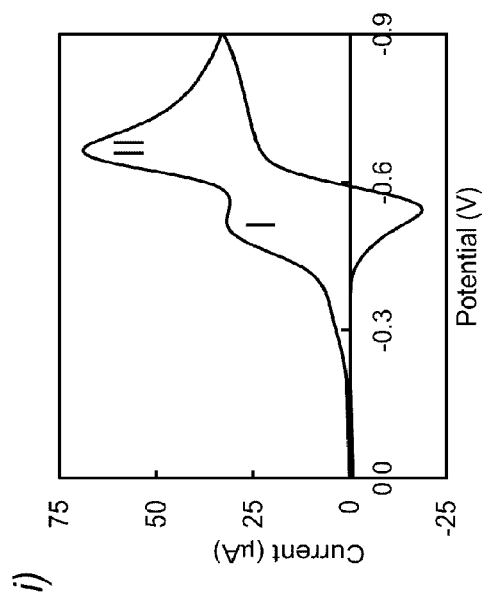
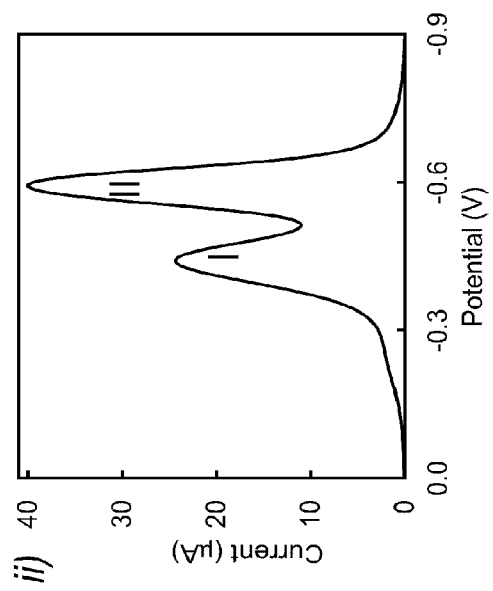

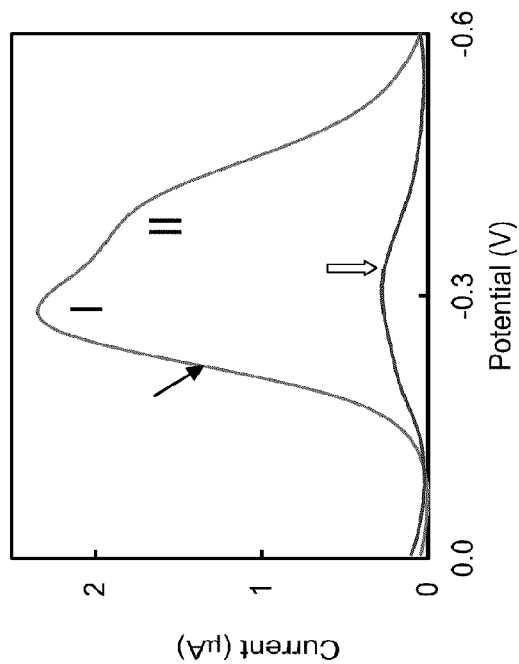
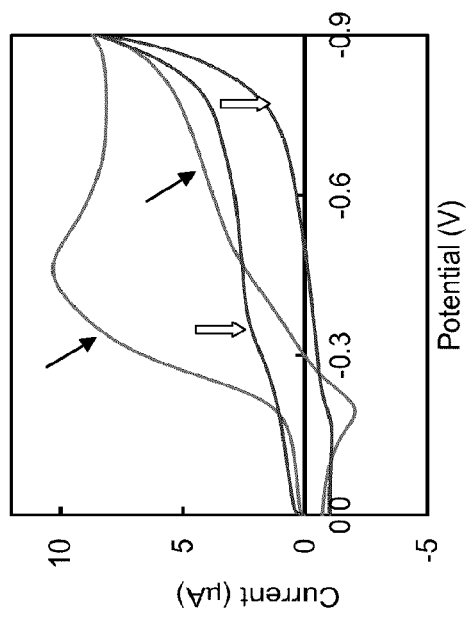
FIG. 7B
FIG. 7A

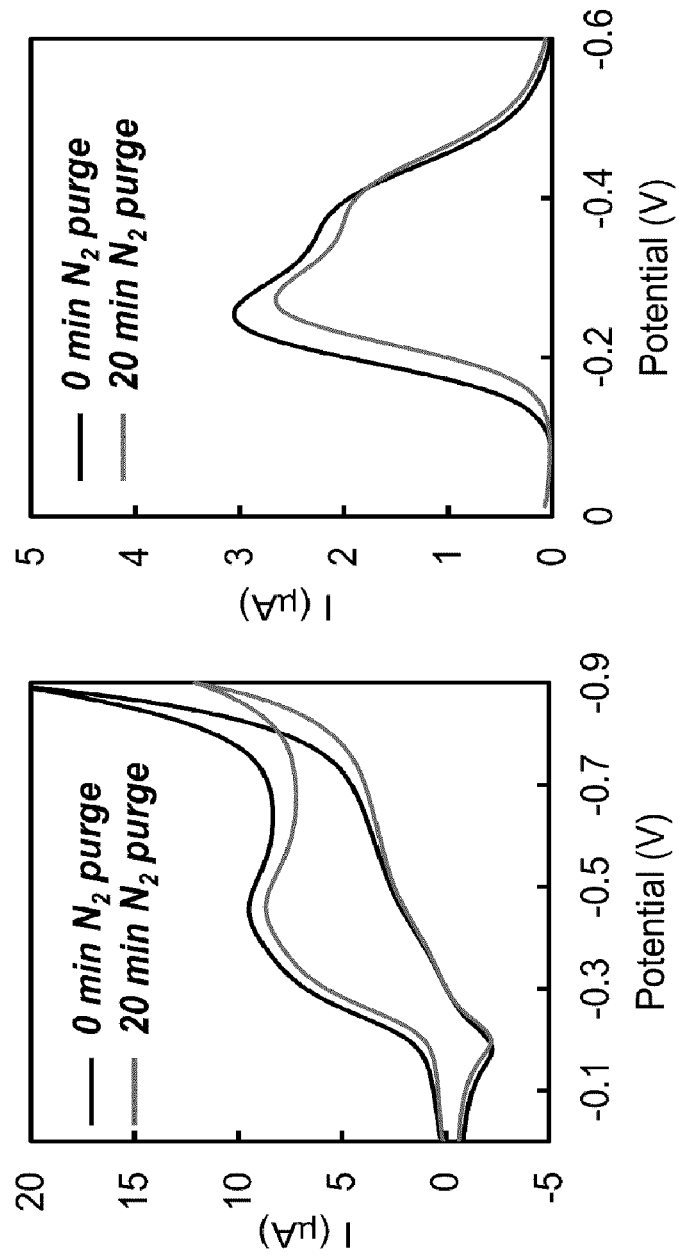

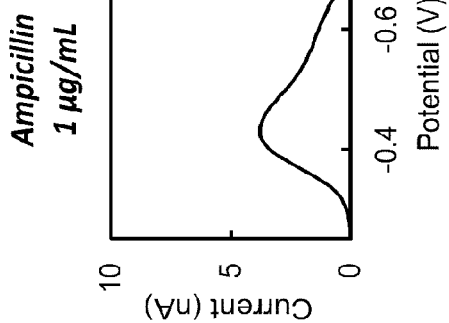
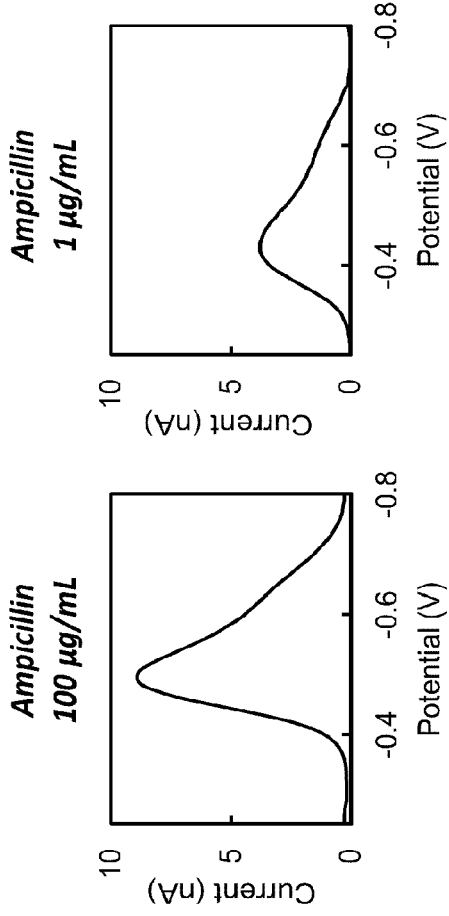
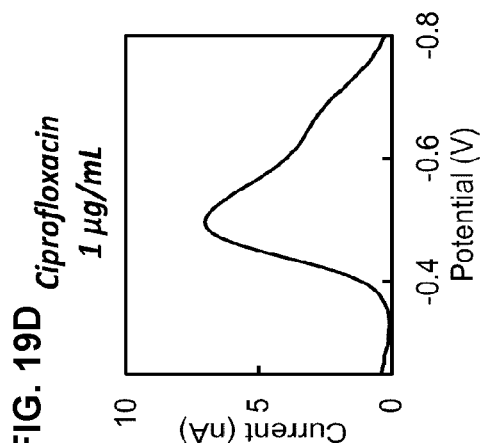
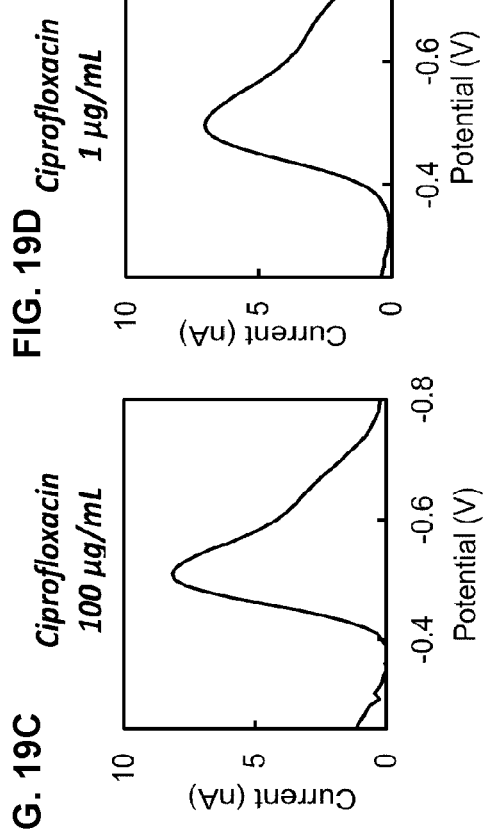
FIG. 19A Ampicillin 100 μg/mL
FIG. 19B Ampicillin 1 μg/mL
FIG. 19C Ciprofloxacin 100 μg/mL
FIG. 19D Ciprofloxacin 1 μg/mL

ELECTROCHEMICAL METABOLIC ACTIVITY DETECTING DEVICE

RELATED APPLICATIONS

This application is a continuation of U.S. patent application Ser. No. 15/523,131; which is the National Stage of International application No. PCT/CA2015/051102, filed Oct. 28, 2015; which claims the benefit of and priority to U.S. provisional patent application No. 62/069,601, filed Oct. 28, 2014; the contents of which are all hereby incorporated by reference as if recited in full herein for all purposes.

FIELD

The present disclosure relates to methods and systems for detecting metabolic activity of targets cells in a sample. In some examples, the present disclosure relates to electrochemical detection of antibiotic susceptibility.

BACKGROUND

The overuse of antibiotics and the prescription of first-line antibiotics to which a pathogen is not susceptible, contribute to rising antibiotic resistance rates, which is a growing threat to public health worldwide.[1] Urinary tract infections are among the most prevalent bacterial infections.[2] Gold-standard antibiotic susceptibility tests for urinary tract infections rely on culture and typically require 1-3 days in order to allow the bacteria to multiply to detectable levels.[3] After pre-culture of the bacteria, an additional 18 hours are typically required to perform standard susceptibility tests. Reducing the time needed to determine the susceptibility profile of urinary tract infections could improve clinical outcomes, especially in the case of the most severe infections that lead to urosepsis.[4] Rapid testing could also contribute to decreased unnecessary antibiotic use,[5] and could increase the efficiency of centralized diagnostic laboratories. Treatment of other infections may similarly benefit from improved susceptibility testing.

Tests for antibiotic resistance that rely on enzymatic amplification of antibiotic-resistance genes have been found to reduce turnaround times compared to culture.[6,7,8,9] Unfortunately, these assays often require a pre-incubation step to allow the bacteria to multiply, and, further, often require several hours to amplify the genes of interest. Gene-based assays are also typically limited by the requirement of knowing a priori which genes confer resistance. Dozens of constantly-evolving genes may be implicated in resistance to a given antibiotic, and it may be impractical to test for all possible mutations simultaneously.[10]

Assays that monitor bacterial viability in response to antibiotics may overcome at least some limitations of genetic tests. These tests report directly on the question of greatest clinical importance: whether a given antibiotic decreases bacterial survival. New assays for antibiotic resistance include the detection of bacterial motion using AFM cantilevers,[11] electrochemical measurements of bacterial growth,[11,12,13,14,15,16] optical detection of bacterial growth,[17,18] and optical detection of redox reporters of bacterial metabolism.[19,20,21,22] In assays that detect metabolically-active pathogens, the bacteria are typically incubated with the antibiotic and a redox reporter of metabolism such as resazurin or methylene blue. Metabolically-active bacteria create a reducing environment and either directly or indirectly reduce the compound, and the change in redox state is read out as a change in color or fluorescence. Resistant bacteria continue to multiply and metabolize the compound, while susceptible bacteria do not.

Successful detection using this type of approach typically hinges on the requirement that a sufficient quantity of the reduced form of the reporter compound accumulates above the detection threshold, a delay that may take at least 12 hours in milliliter-scale culture.[19] Strategies have been proposed that seek to confine bacteria in microliter and nanoliter volumes with the goal of reducing the time of detection by increasing the local concentration of the bacteria.[20,21,23,24,25] In the most sensitive of these optical techniques, the sample is divided into millions of nanoliter droplets and the signal is readout sequentially from each droplet with a high-powered fluorescence microscope.[20,21,25] Despite the increase in local effective concentration provided by this approach, several hours are typically still required for analysis. Moreover, many of these devices only detect the presence or absence of a pathogen and not its antibiotic susceptibility profile.[25,26,27]

SUMMARY

In some examples, the present disclosure describes a device suitable for detecting metabolic activity of target cells in a sample. The device includes: a nanoliter well including: an inlet for receiving the sample; a microfilter for inhibiting the target cells from exiting the well through an outlet of the well; and electrodes in the well for sensing an electrochemical state of contents in the well.

In some examples, the device may further include: a plurality of the wells.

In some examples, the present disclosure describes a method for detecting metabolic activity of target cells in a sample. The method includes: concentrating the target cells in a nanoliter well; introducing into the well a reporter compound that exhibits a change in electrochemical state in response to metabolic activity of the target cells; determining any change in an electrochemical state of contents in the well over a time period; and detecting metabolic activity or viability of the target cells based on a determined change in the electrochemical state of contents in the well.

BRIEF DESCRIPTION OF THE DRAWINGS

Reference will now be made, by way of example, to the accompanying drawings which show example embodiments of the present application, and in which:

FIG. 4 is a chart illustrating electrochemical measurement of bacterial viability using an example of the disclosed device;

FIGS. 6A and 6B show cyclic voltammograms and differential pulse voltammograms in different buffers;

FIGS. 7A and 7B are charts showing electrochemical changes in resazurin due to reduction by bacteria;

FIGS. 8A and 8B are charts illustrating the effect of dissolved oxygen on the electrochemistry of resazurin;

FIGS. 19A-19D are charts showing representative electrochemical scans acquired using the example device after introducing *E. coli* spiked in urine and resazurin and an antibiotic;

Similar reference numerals may have been used in different figures to denote similar components.

DESCRIPTION OF EXAMPLE EMBODIMENTS

Despite several recent advances in ultrasensitive electrochemical detection of bacteria,[28,29,30] few devices have been reported for direct electrochemical detection of antibiotic resistance. Electrochemical readout typically requires only simple electronics, which may allow direct electronic detection of antibiotic susceptibility from confined nanoliter droplets without bulky optical instrumentation for readout.

The present disclosure describes example methods and devices for electrochemical detection of metabolic activity of biological agents, such as bacteria. Examples of the present disclosure may be used to help identify the antibiotic susceptibility profile of bacteria. The present disclosure describes development of an example assay that may use electrochemical readout to detect metabolically active bacteria. In examples described herein, the electrochemical reduction of a reporter compound, such as resazurin, is monitored to establish the presence of live bacteria, and further may be analyzed in the presence of antibiotics to determine resistance profiles.

In various examples discussed herein, resazurin may be used as the reporter compound. Generally, the reporter compound may be any compound that exhibits an electrochemical change (e.g., change in oxidation state) in response to metabolic activity of the cells of interest (e.g., bacteria). For a given concentration or amount of the reporter compound, the degree to which the electrochemical state of the reporter compound has changed over a given time period may be indicative of the metabolic activity of the cells of interest. The reporter compound may be resazurin, methylene blue, formazan, or tetrazolium salts, or any other compound having a redox response to metabolic activity of the target cell.

Figure 1A:
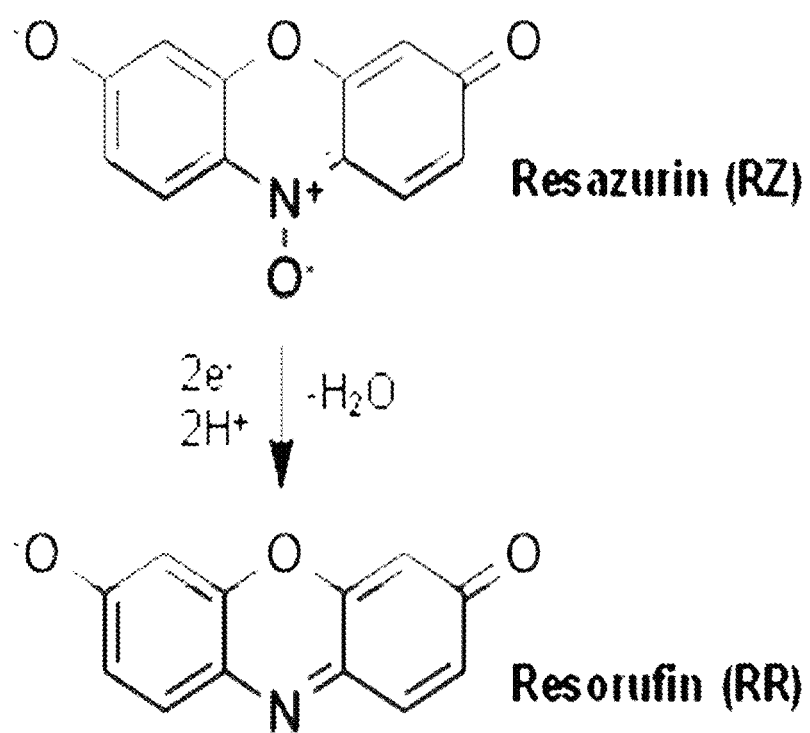
FIG. 1A shows the process of resazurin being reduced to resorufin.

Redox dyes that are reduced by metabolically-active bacteria have been used as optical indicators of bacterial viability in the presence of antibiotics,[19] but have not offered significant improvement in the delivery of rapid profiling results. In the present disclosure, resazurin, a commonly-employed reporter used to optically assess cell viability,[19] may be used for electrochemical detection of bacterial antibiotic susceptibility. FIG. 1A shows the process of resazurin (RZ) being reduced to resorufin (RR) by metabolically active bacteria.

When implemented using the disclosed device, the sensitivity of this readout method may produce improvements in assay speed. Although examples described herein use resazurin as a reporter compound, other compounds that have an electrochemical change (e.g., change in oxidation state) in response to metabolic activity of the target bacterial (or other target cell) may be used.

In the presence of an ineffective antibiotic, resistant bacteria will continue to multiply and create a reducing environment which converts resazurin to resorufin. On the other hand, since effective antibiotics hinder bacterial metabolism, they will prevent or inhibit reduction of the dye by susceptible bacteria. As resazurin and resorufin have different electrochemical signatures (as discussed below),[31,32] using differential pulse voltammetry it is possible to distinguish between the two electrochemical states of the dye and thus determine whether the bacteria is susceptible.

FIGS. 6A and 6B are charts showing electrochemical characterization of resazurin. The example data shown in FIGS. 6A and 6B were acquired using an Au macroelectrode and a Ag/AgCl reference electrode. FIG. 6A shows cyclic voltammograms (i) and differential pulse voltammograms (ii) of 10 mM resazurin in PBS+20% ACN. FIG. 6B shows cyclic voltammograms (i) and differential pulse voltammograms (ii) of 10 mM resazurin in LB media. When resazurin is present in aqueous buffer, the initial irreversible two-electron reduction of the dye to resofurin occurs at −0.35 V vs Ag/AgCl. An additional reversible process is observed at −0.6 V that represents the two electron reduction of resofurin to dihydroresofurin.[31,32] As FIGS. 6A and 6B demonstrates, the reduction of resazurin to resorufin may be detected as a change in electrical characteristics.

FIGS. 7A and 7B are charts showing electrochemical changes in resazurin due to reduction by bacteria. The example data shown in FIGS. 7A and 7B were acquired using an Au macroelectrode and a Ag/AgCl reference electrode. FIG. 7A shows cyclic voltammograms (CVs) of *E. coli* at $1\times10^6$ CFU/mL before (black arrows) and after (white arrows) incubating with 1 mM resazurin for 6 hrs at 37° C. in LB media. FIG. 7B shows corresponding differential pulse voltammograms (DPVs). In bacterial culture media at 37° C., the formation of dihydroresofurin occurs at a less negative potential and is visualized as a shoulder on the resazurin reduction peak when differential pulse voltammetry (DPV) is used to monitor the redox reporter. Nonetheless, a significant decrease in the electrochemical signal is observed in the presence of active bacteria.

FIGS. 8A and 8B are charts illustrating the effect of dissolved oxygen on the electrochemistry of resazurin. Shown are CVs (FIG. 8A) and DPVs (FIG. 8B) acquired using a gold macroelectrode with 1 mM resazurin in LB media before and after purging with $N_2$ for 20 min. A 13% decrease in the DPV peak current was observed after purging with $N_2$. These results indicate that any redox reaction of dissolved oxygen did not significantly affect the electrochemical measurements.

The above characterization of resazurin illustrates the suitability of this compound as an indicator of bacterial metabolic activity. In examples described herein, this characteristic of resazurin may be used as the basis of methods and devices for detecting susceptibility of bacteria to antibiotics.

Figure 1B:
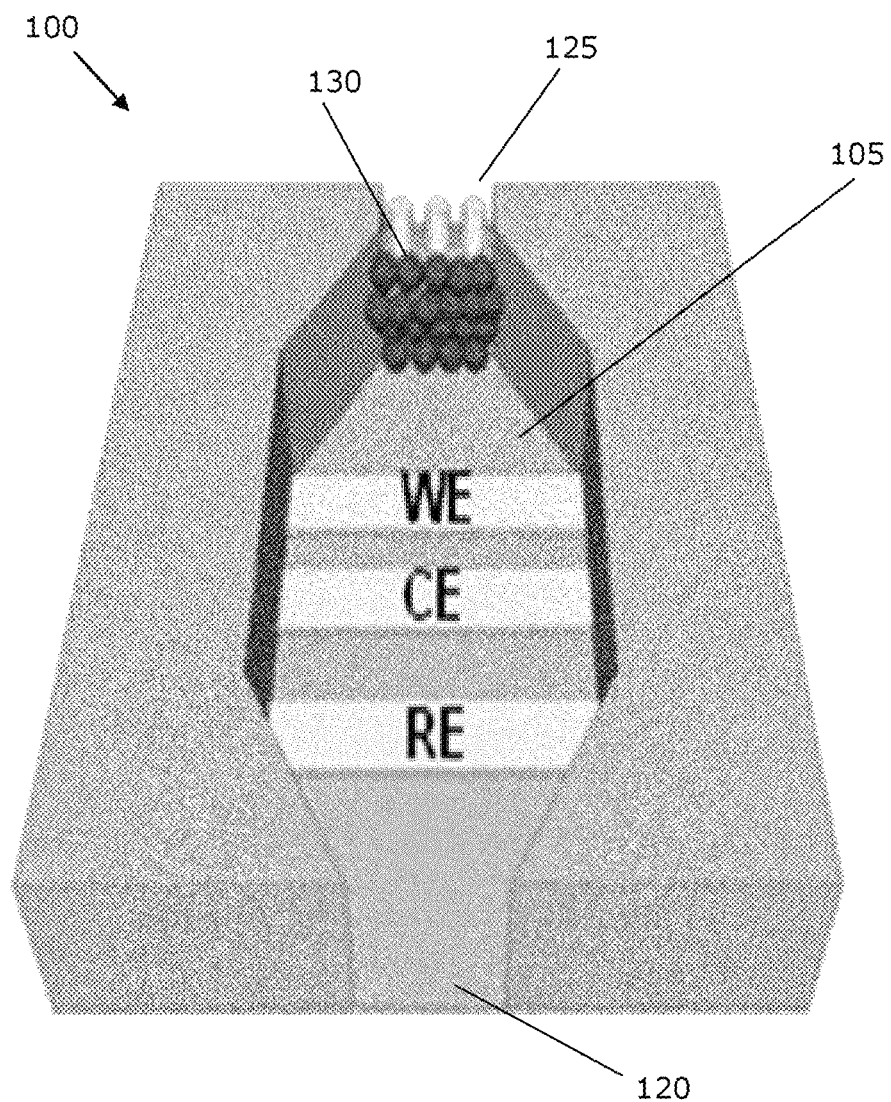
FIGS. 1B and 1C are schematics of examples of the disclosed device.

FIG. 1B is a schematic of an example device 100 for detecting metabolic activity of target cells, such as bacteria. The device 100 includes a well 105 with a small volume (e.g., a nanoliter well) in which a sample to be tested may be received. The well 105 may contain electrodes for obtaining electrochemical measurements. As shown, the well 105 may include a working electrode (WE) and a counter electrode (CE). In some examples, the well 105 may additionally include a reference electrode (RE), which may be useful for obtaining more consistent and/or reliable measurements. The electrodes may enable a readout of bacterial metabolism. The well 105 may be provided with a well inlet 120 and a well outlet 125. The well 105 also contains an integrated microfilter 130 positioned near the well outlet 125 for bacterial capture. As described further below, the filter 130 may be formed by packed microbeads over a small outlet opening (e.g., a grate or a small gap). Bacteria may be cultured in each well 105. In some examples, the filter 130 may instead be provided by a material having micropores (e.g., a semi-permeable membrane), or other suitable arrangements. Although FIG. 1B illustrates the filter 130 located at the well outlet 125, the filter 130 may be positioned at any other location, as long as the filter 130 is able to capture target cells within the cell 105. For example, the filter 130 may be provided closer to the well inlet 120 and trap the target cells close to the well inlet 120 instead.

Figure 1C:
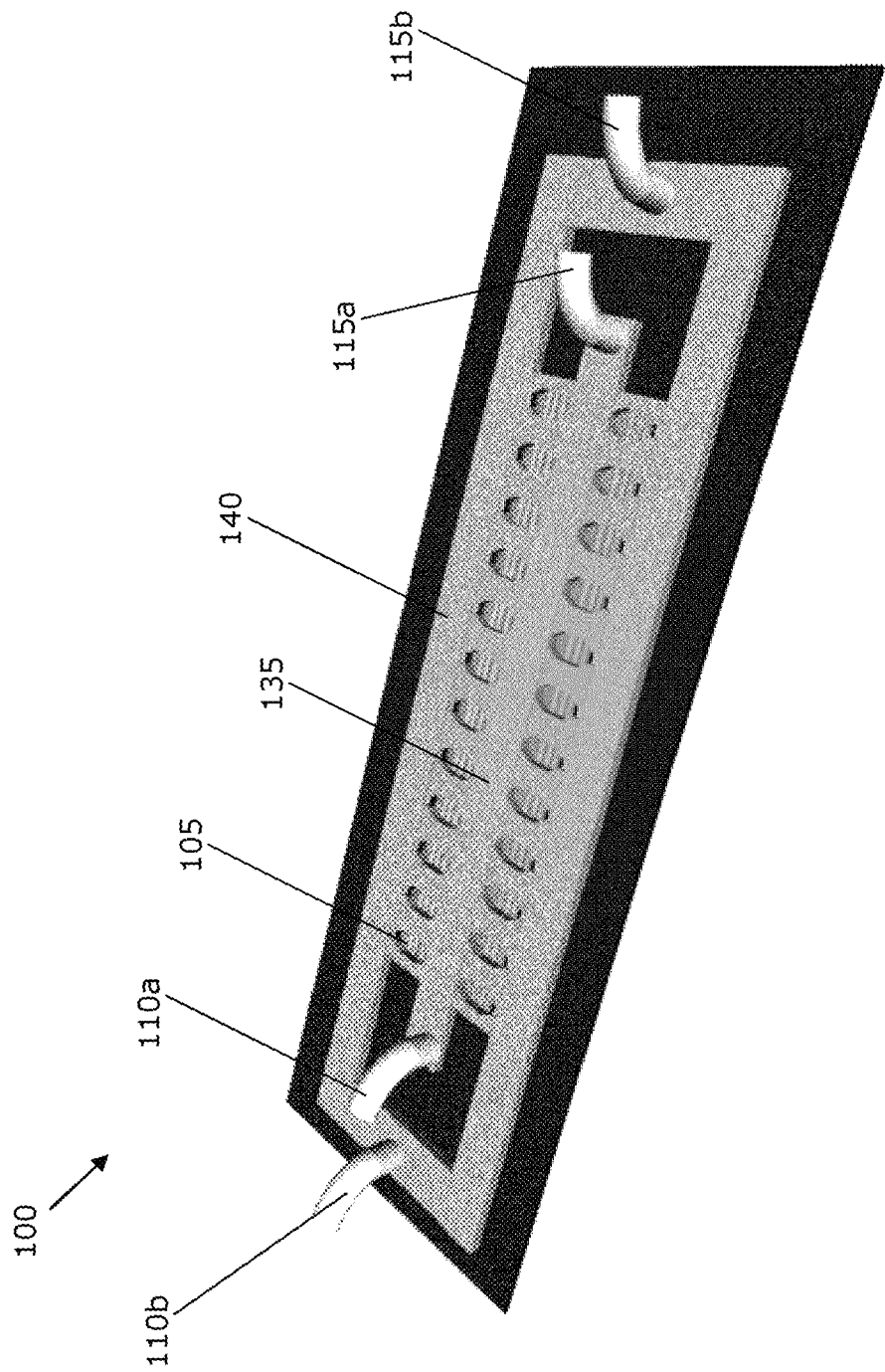

FIG. 1C is a schematic of another example device 100 for detecting metabolic activity. The example device 100 of FIG. 1C may contain a plurality of sensor wells 105. In the example shown, the device 100 includes an inner channel 135 and an outer channel 140. The inner channel 135 has an inlet 110a for receiving a test sample, and an outlet 115a for removing waste; similarly the outer channel 140 has an inlet 110b and an outlet 115b. The inner and outer inlets 110a, 110b may be collectively referred to as inlets 110, and the inner and outer outlets 115a, 115b may be collectively referred to as outlets 115. In the example shown in FIG. 1C, the inner and outer channels 135, 140 enable flow to be introduced past both the well inlets 120 and the well outlets 125.

Figure 20:
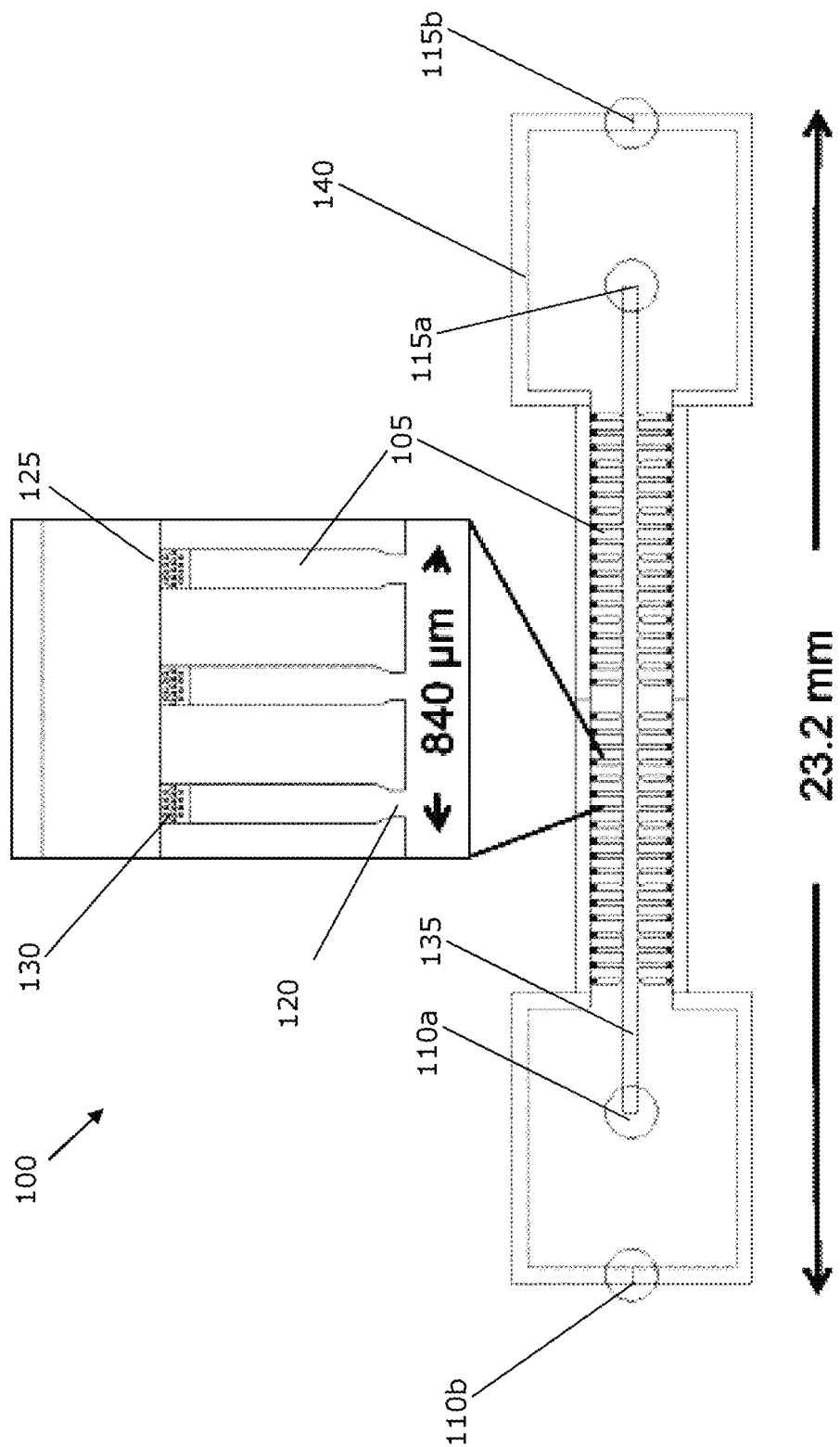
FIG. 20 is a schematic of another example of the disclosed device.
Figure 21:
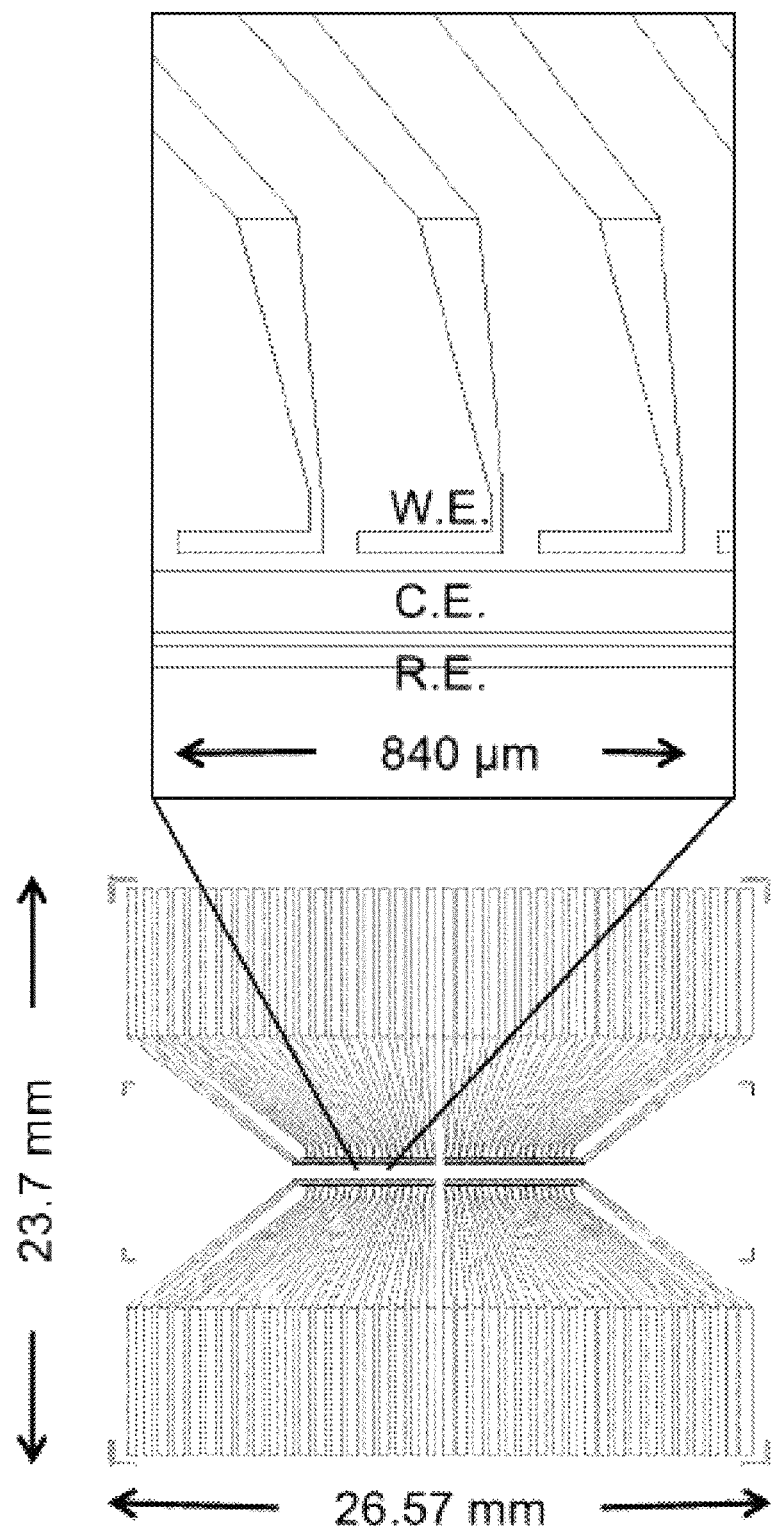
FIG. 21 is an electrode layer that may be used in an example of the disclosed device.

FIG. 20 shows another example device 100, similar to the example device 100 of FIG. 1C. FIG. 21 shows an example of an electrode array that may be patterned for use with the multi-well design of FIG. 20. FIG. 21 shows an electrode array for wells 105 that include reference electrodes (RE) in addition to the working electrodes (WE) and counter electrodes (CE). FIGS. 20 and 21 provide example dimensions for the device 100, however such dimensions are not intended to be limiting.

Figure 1D:
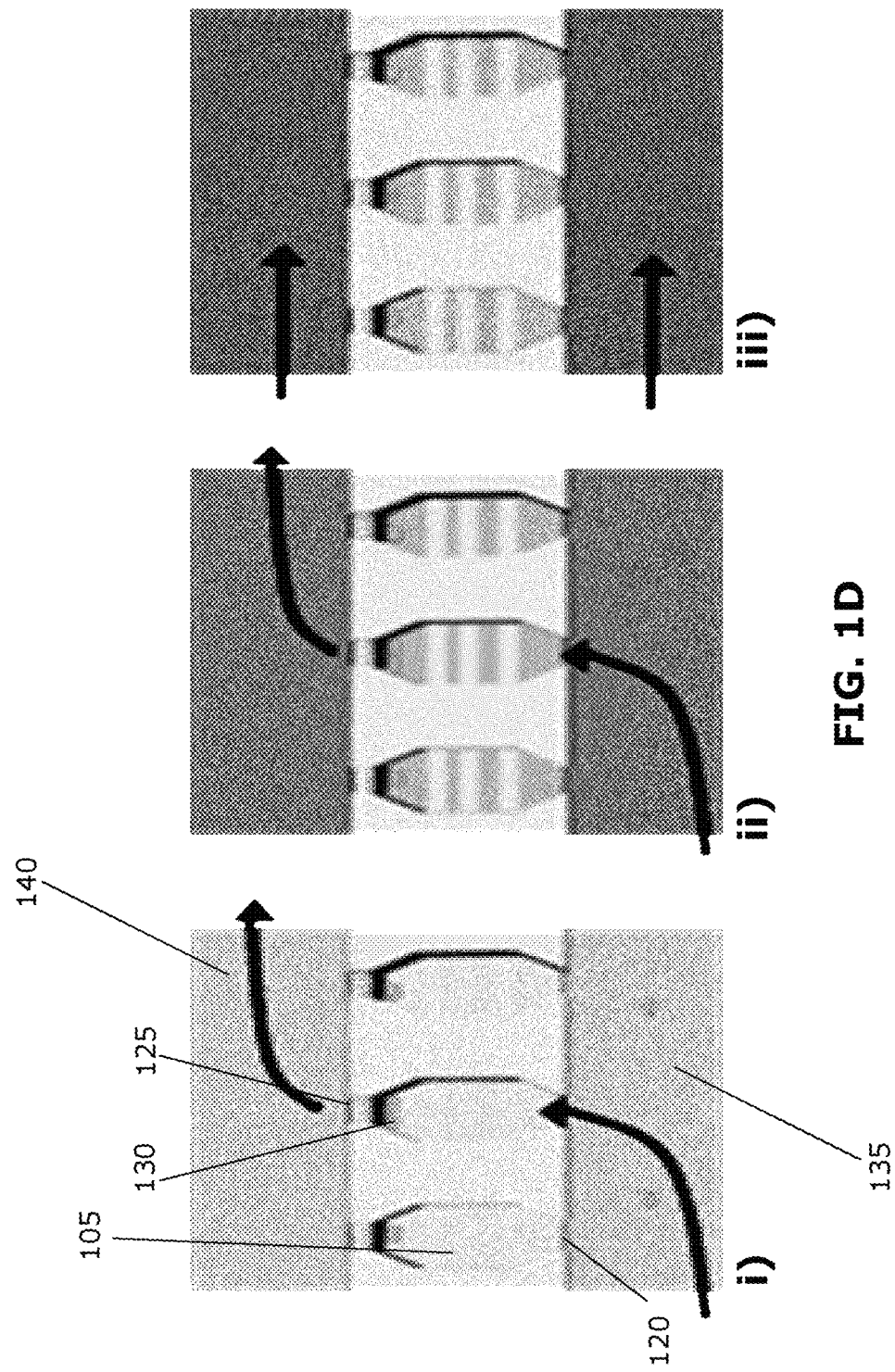
FIG. 1D illustrates an example operation of the disclosed device.

FIG. 1D shows an example of how the example device 100, having a plurality of wells 105, may be used. A test sample (e.g., a urine sample), possibly containing target cells (e.g., bacteria), may be introduced into the device 100 via the inner inlet 110a. The sample passes through the wells 105 and any bacteria are prevented from leaving the well 105 by the filter 130 of the well 105, thus capturing the bacteria within the well 105 while the solution is able to pass through the filter 130 to exit the device 100 (see FIG. 1Di). The reporter compound (e.g., resazurin) and a culture media may then be introduced to the wells 105 in a similar manner (see FIG. 1Dii). If the device 100 is being used to detect for antibiotic susceptibility, an antibiotic may also be introduced at this time. Plugs are formed within wells by introducing an immiscible oil (e.g., a fluorinated oil such as FC-40) in the inner and outer channels 135, 140, passing across the well inlets 120 and well outlets 125 (see FIG. 1Diii). The oil displaces the aqueous solution in the main channels. Due to surface tension, a sealed nanoliter plug of culture media remains in each well. Other methods of plugging the wells 105 may be used. For example, introduction of air bubbles may be used to plug the wells 105. In some examples, each well 105 may be provided with controllable valves (e.g., mechanical or pressure-based valves) at the well inlets 120 and well outlets 125, and the valves may be controlled to be open when introducing the sample, reporter compound and culture media, and to seal off each well 105 afterwards, instead of using plugs. If valves are used instead of oil plugs, it may not be necessary to have inlets 110a, 110b and outlets 115a, 115b for inner and outer channels 135, 140, which may help to simplify the design of the device 100. In some examples, a combination of plugs and valves may be used (e.g., using oil plugs to seal off well outlets 125 and valves to seal off well inlets 120).

In general, by sealing off the well inlets 120 and outlets 125 (e.g., using oil plugs, valves or a combination thereof), the contents of each well are isolated. By restricting the solution volume to that of the well, after trapping the target cells, the effective concentration of the target cells is increased.

Figure 1E:
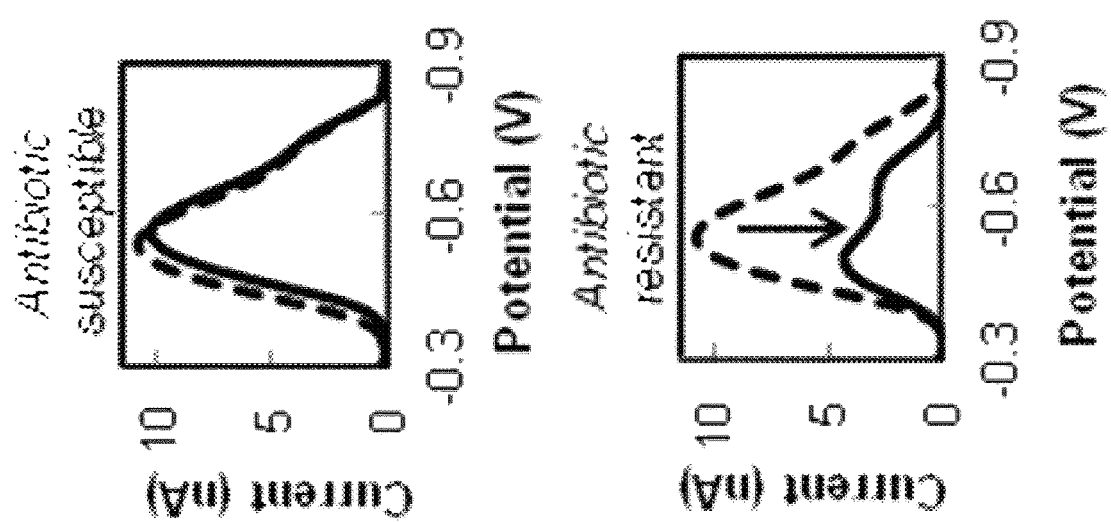
FIG. 1E show example differential pulse voltammograms illustrating the principle of electrochemical phenotyping for detecting antibiotic susceptibility.

The device can then be incubated at 37° C. to allow the captured bacteria to multiply. The reporter compound will exhibit a change in electrochemical state if there are metabolically active target cells in the well. For example, if testing for antibiotic susceptibility of bacteria and using resazurin as the reporter compound, then antibiotic-susceptible bacteria captured within a well 105 will exhibit decreased or no metabolic activity (e.g., inhibited from reproducing) due to the presence of the introduced antibiotic, while resistant bacteria will exhibit greater metabolic activity (e.g., continue to multiply unhindered) compared to the antibiotic-susceptible bacteria. Accordingly, the antibiotic-resistant bacteria will reduce the resazurin to a greater extent than the antibiotic-susceptible bacteria (e.g., the antibiotic-susceptible bacteria may not reduce resazurin at all while the antibiotic-resistant bacteria will). The degree to which reduction has occurred can be distinguished by measuring the current using the electrodes in each well 105. FIG. 1E show example differential pulse voltammograms (DPVs) illustrating the principle of electrochemical phenotyping described above.

Figure 10A:
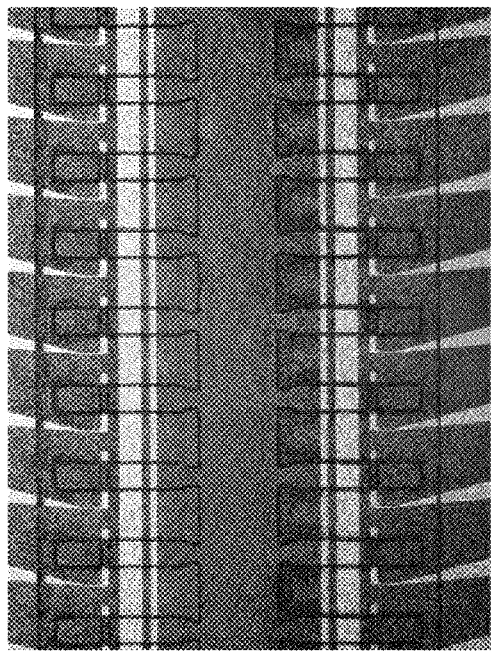
FIGS. 10A and 10B show optical images of an example of the disclosed device.
Figure 10B:
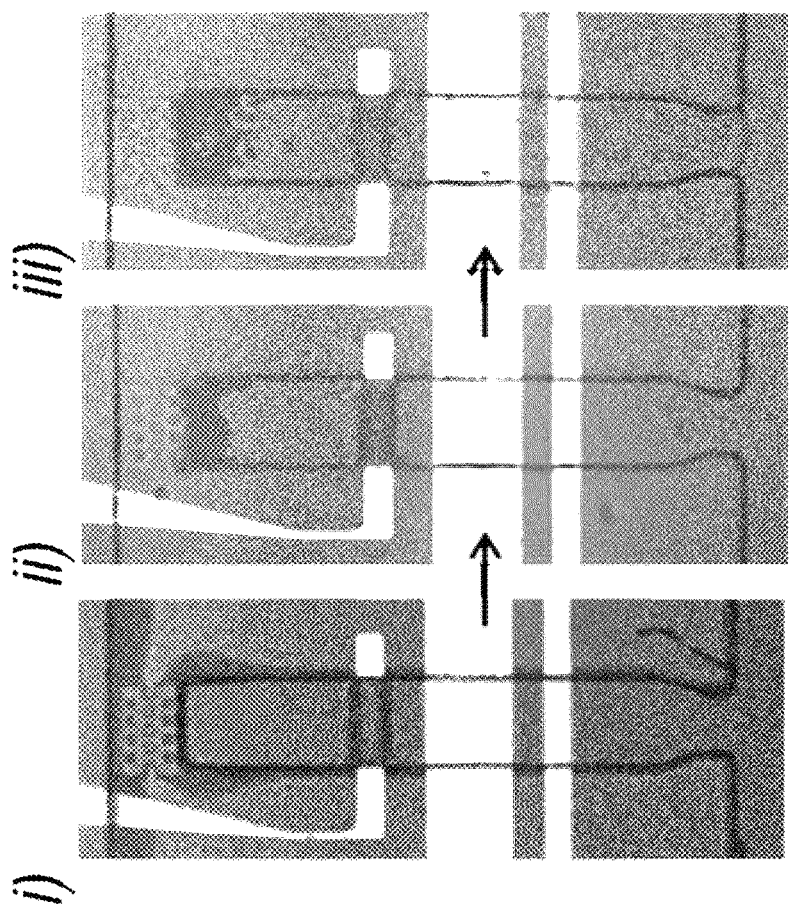

FIGS. 10A and 10B show optical images of the example device. FIG. 10A is an optical image of a portion of the well array. FIG. 10B are optical images of a single well, showing the process described with respect to FIG. 1D above. At FIG. 10Bi, the well is clear of bacteria. At FIG. 10Bii, microbeads are introduced into the well and are trapped by a barrier that defines small openings at the outlet of each well. The microbeads may function, together with the barrier, as the filter for capturing bacteria. In some examples, it may not be necessary to introduce microbeads, such as where the barrier fabricated into the well is sufficient to capture the target cells within the well. At FIG. 10Biii, bacteria from the introduced test sample are captured in the well. A nanoliter plug is then formed by introducing an immiscible organic phase.

As discussed further below, in some examples, the disclosed device may be used to detect a clinically relevant concentration of bacteria with a relatively short (e.g., 30 minute) incubation. In examples discussed below, it may be shown that the antibiotic susceptibility profile of a clinically-relevant concentration of bacteria in urine can be determined using a 1 hour incubation without a pre-incubation step. Thus, examples of the present disclosure may enable antibiotic resistance phenotyping on a relatively short time scale.

In some examples, the disclosed device may enable a decrease in detection time, to improve the clinical utility of reporter compounds such as resazurin as an indicator of metabolic activity. In examples of the disclosed device, the target cells (e.g., bacteria) may be concentrated in a nanoliter well. By conducting the resazurin assay within this small volume, the time required to detect the presence of viable bacteria was found to be reduced to less than one hour. The integration of electrochemical sensors (e.g., electrodes) directly into each of the wells may allow for relatively rapid and direct readout of the antibiotic susceptibility profile in a relatively small volume, without requiring bulky optical instrumentation to sequentially readout thousands of nanoliter droplets.

The present disclosure may provide advantages over conventional approaches. By concentrating the bacteria inside miniaturized wells, the local effective concentration of the bacteria may be increased. For example, 10 bacteria captured in a 1 nL well is equivalent to 10 000 cfu/µL, while 10 bacteria captured in 1 µL well gives a concentration of only 10 cfu/µL. The greater the concentration of bacteria per well, the faster the turnover of resazurin and accumulation of the target redox molecule. As the signal from DPV is directly proportional to the concentration of the redox molecule, an increase in local concentration of bacteria increases the magnitude of the signal change acquired, and hence easier and/or quicker detection. Confinement of the assay within a nanoliter volume may provide another advantage. As resazurin is reduced, it is prevented from diffusing into bulk solution, thus allowing the reduced form to rapidly accumulate to detectable levels.

In examples discussed herein, the device may be configured with wells having dimensions of about 100 µm×50 µm×550 µm, which is equivalent to a volume of about 2.75 nL. By providing a plurality of such wells in a single example device, multiple measurements (e.g., one from each well) may be obtained per single sample, which may help to increase the accuracy of the device. For example, 15 measurements may be performed per sample. A single measurement from a given well may vary from the mean measurement by as much as 40%. However, the standard error after 15 measurements may be reduced to as little as 5%. In some examples, additionally, each well may include a plurality of working electrodes, to obtain multiple measurements from each well, which may be averaged for each well.

Example Fabrication

An example process for fabricating the example disclosed device is now discussed. Fabrication may be performed by patterning gold electrodes on a glass substrate to act as the working, counter and reference electrodes.

Figure 11:
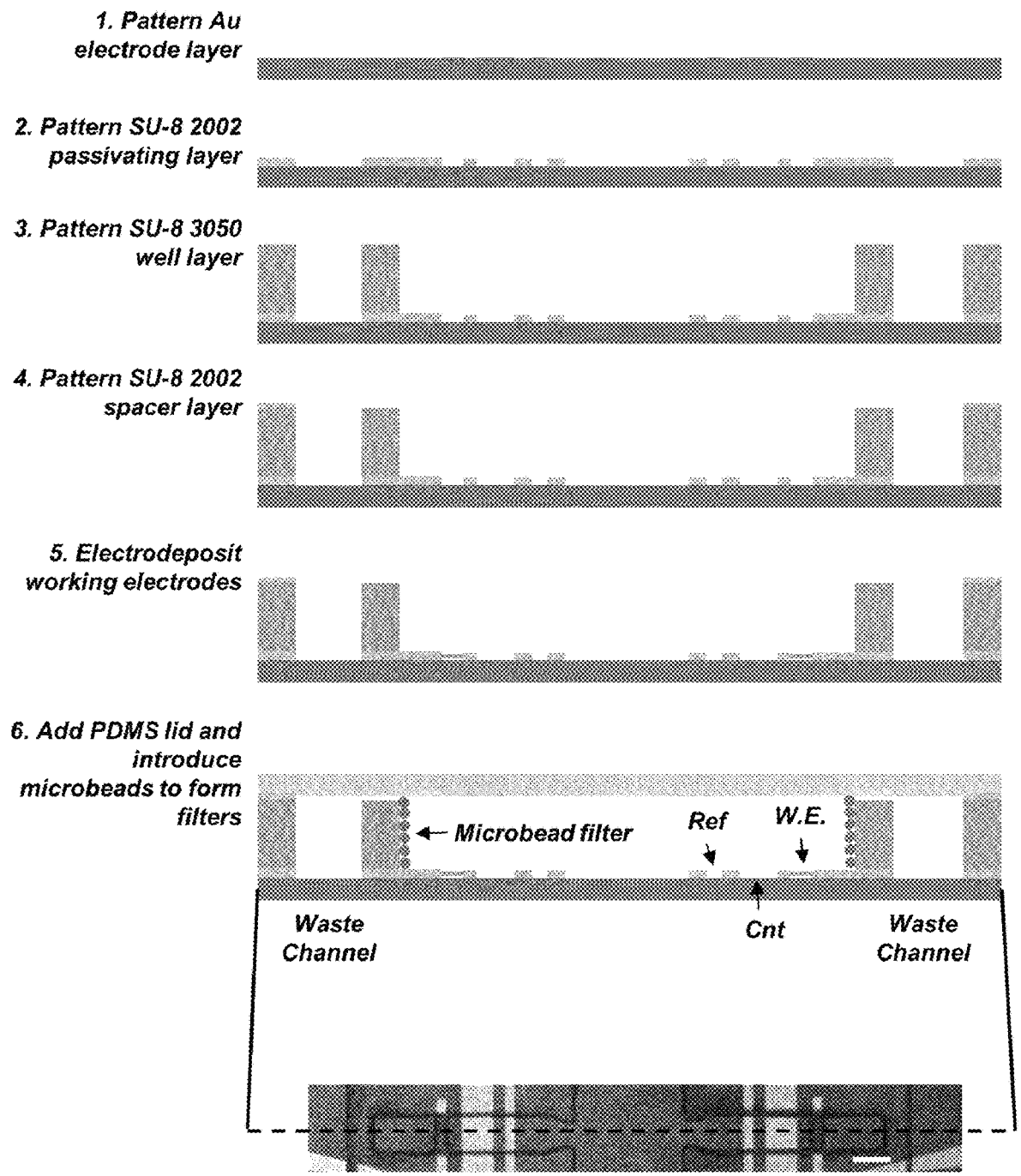
FIG. 11 schematically illustrates an example fabrication method for an example of the disclosed device.

FIG. 11 schematically illustrates steps in an example fabrication process for an example of the disclosed device. FIG. 11 shows the example fabrication process viewed at a cross-section of a multi-well device, and illustrates the fabrication of two opposing wells. At 1, the electrode layer is formed. In this example, a gold layer (e.g., 100 nm in thickness) is patterned using standard photolithography. Cr may be used as an adhesion layer. Next, at 2, the patterned electrodes are passivated, for example using 2 µm of SU-8 2002 using photolithography. At 3, a well layer (e.g., 50 µm thick) may then be patterned, to define the well(s) of the example device, for example using SU-8 3050. At 4, a second layer of SU-8 2002 may then be patterned as a thin (e.g., 2 µm) spacer, creating a thin gap between the well layer and the later applied device top. This gap may serve as the small opening at the outlet of the well. It was experimentally determined that a gap of 2 µm may be too large to trap bacteria efficiently. However, this gap may be designed to be small enough to trap the microbeads (e.g., 5 µm in diameter) used for the microfilter. In some examples, where the target cells are sufficiently trapped by the fabricated gap, or where the gap (or other structural feature, such as a grate) is fabricated to be sufficiently small, it may not be necessary to introduce microbeads. In some examples, other materials (e.g., a microporous membrane) may be used instead of microbeads for the microfilter. To increase the surface area of the electrodes, at 5, gold may then be electrodeposited on the working electrodes, for example by applying −300 mV for 30 s with respect to an Ag/AgCl reference electrode in a solution of 50 mM $HAuCl_4$ and 0.5 M HCl. Finally, at 6, the device may be capped with a polydimethylsiloxane (PDMS) lid. The PDMS lid may include holes for the inlets and outlets. The PDMS lid may be bonded to the top of the device after an oxygen plasma treatment for 30 s.

The fabricated device may be further processed, for example to remove air bubbles. For example, prior to use, the device may be filled with EtOH and flushed with phosphate buffered saline (PBS). In this example, 100 µL of microbeads (Sigma Aldrich, St. Louis, Mo.) with a 5 µm diameter diluted 1:100 in PBS were introduced at 10 µL/min to form the in-well filters.

Example Studies

Various example studies were carried out to characterize and investigate performance of the example device discussed above.

Figure 12A:
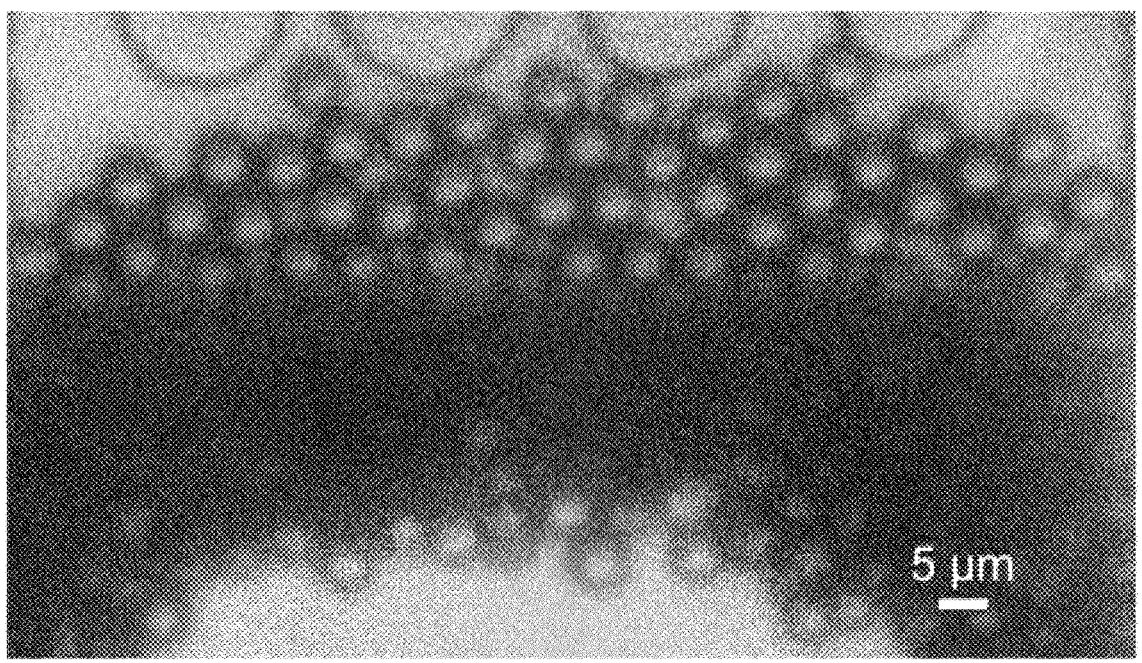
FIGS. 12A and 12C are example optical images of microbeads forming the microfilter in an example of the disclosed device.
Figure 12B:
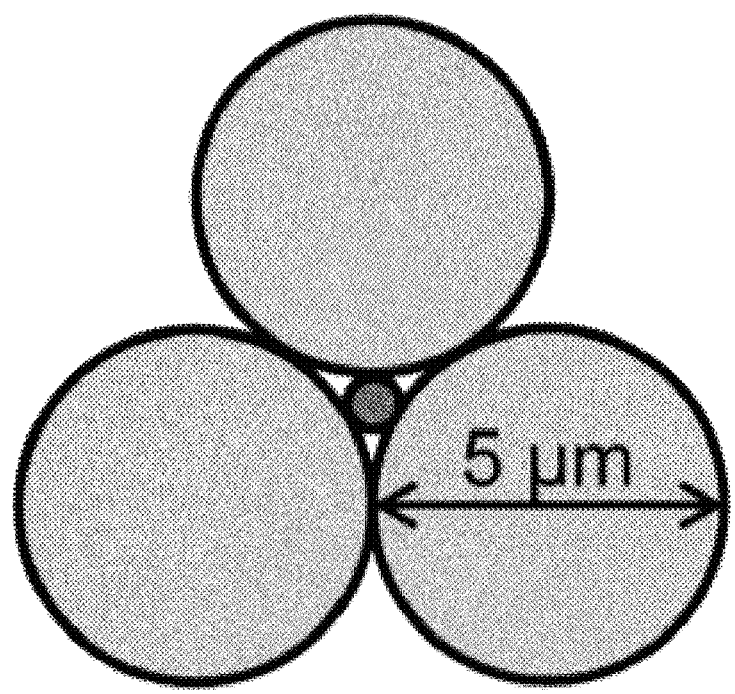
FIG. 12B is a schematic illustrating hexagonal close packing of spheres.
Figure 12C:
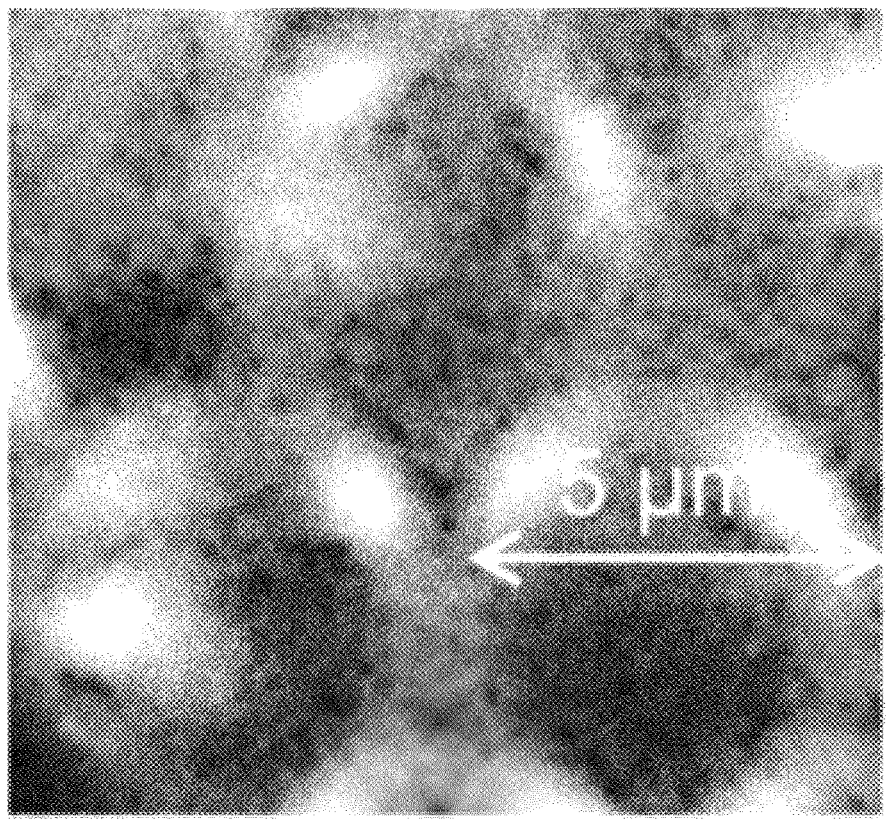

The pore size of the in-well filters, in these examples using microbeads, may be characterized. As the microbeads are substantially spherical, equations pertaining to the packing of spherical objects may be useful. The densest possible packing of spheres is hexagonal close packing, illustrated in FIG. 12B. In this arrangement, the packing fraction is 0.74 and the pore diameter is given by[1]:

$$D_p=0.154D_s$$

where $D_p$ is the diameter of the pores and $D_s$ is the diameter of the spheres. For 5 μm diameter beads, assuming hexagonal close packing, the pore diameter is 0.77 μm (represented by the small dark circle in FIG. 12B) which is expected to be sufficiently small to trap a bacterium (which is typically ~1 μm in diameter). In non-ideal packing, the spheres would be expected to pack in an assembly close to random close packing which has a slightly looser packing with a packing fraction of 0.637, which causes a distribution in pore sizes, but does not change the diameter of the smallest pores.[1] This calculation is consistent with the high resolution images shown in FIGS. 12A and 12C. FIG. 12A is an example image of the microbead bed acquired using optical microscopy. FIG. 12C is an example optical microscope image showing a close up of the beads. The pore size in these images was found to be approximately 0.8 μm which is consistent with the calculations discussed above. Other microbead sizes may be used as appropriate for capturing larger or smaller target cells.

Figure 12D:
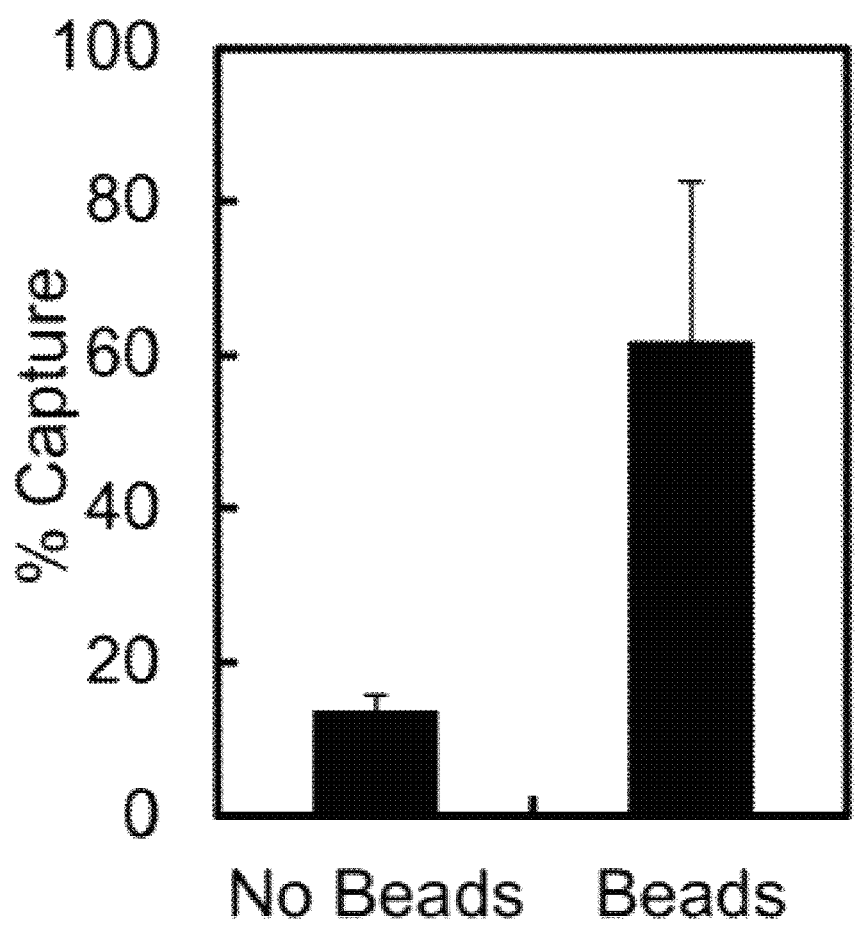
FIG. 12D shows a chart comparing capture rate of *E. coli* with and without the use of microbeads.

To verify the utility of the microbeads for capturing bacteria in the wells, capture efficiency of bacteria was measured for wells with and without microbead filters. FIG. 12D shows a chart demonstrating that, when microbeads are not used, bacteria (in this case, *E. coli*) are captured with low efficiency (less than 20%), compared to about 60% efficiency when microbeads are used. Thus, the use of microbeads in forming the in-well filters may help to concentrate and capture bacteria in the wells.

Figure 12E:
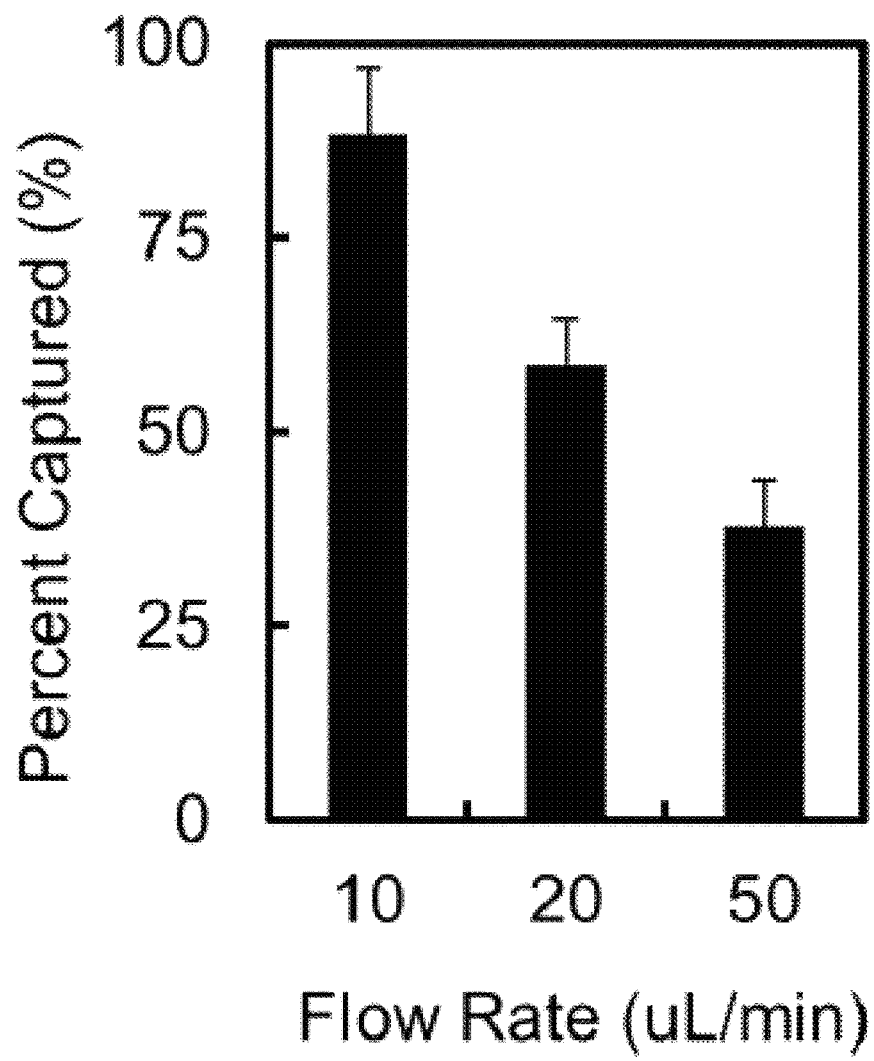
FIG. 12E is a chart illustrating the capture efficiency of *E. coli* was as a function of flow rate.

As the microbeads assemble randomly, there is expected to be a distribution of pore sizes, which may allow some bacteria to escape the filter. Accordingly, the capture efficiency of *E. coli* was also investigated as a function of flow rate. Example results are shown in FIG. 12E. The capture efficiency was found to decrease as a function of flow rate. In the case of the 100 cfu/μL sample, given that there are 72 wells in the example device, each well captured an average of 120 bacteria. Considering that each well has a volume of 2.5 nL, this represents an effective concentration of approximately 50,000 cfu/μL. This represents a 500-fold concentration enhancement above the initial introduced concentration of 100 cfu/μL.

Figure 13:
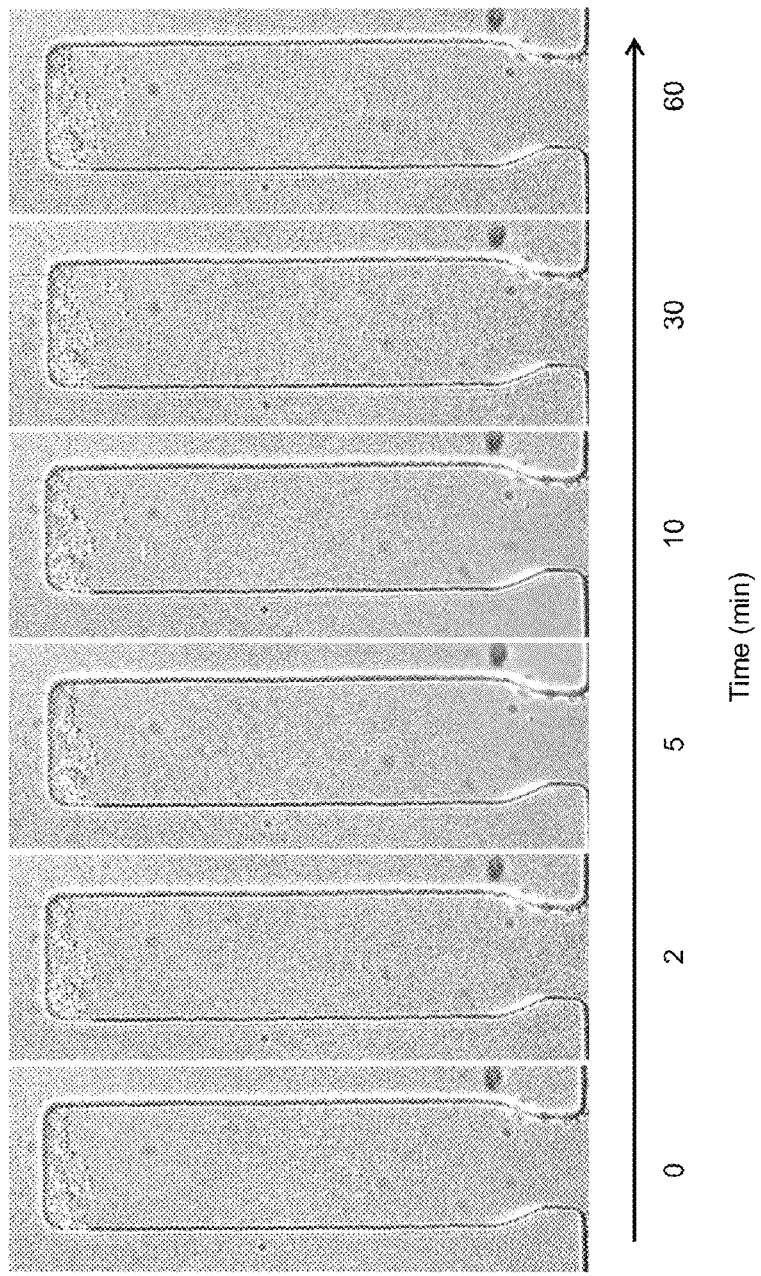
FIG. 13 is a series of optical images showing the stability of the microbeads in an example of the disclosed device.

To measure the stability of the microbead filters, 100 μL of microbeads was injected at 20 μL/min into a test version of the device without the in-well electrodes. The outer-channel inlet and the inner-channel outlet were blocked, forcing the fluid through the wells. After stopping the flow, microscope images were acquired over the course of 1 hour. Examples of these images are shown in FIG. 13. It was found that the microbeads were stable over the course of 1 hour. Although a few beads did become dislodged from the filters, this is not expected to affect the electrochemical measurements as the electrodes are offset by 200 μm from the filter.

In some examples, the filter may comprise microbeads of different sizes, which may be useful to decrease the pore size of the filter. For example, microbeads may be introduced in decreasing sizes (e.g., 5 μm microbeads are first introduced, then 2 μm microbeads), in order to achieve pore size smaller than using a single microbead size, while ensuring that smaller sized microbeads do not inadvertently wash out of the well.

Figure 14:
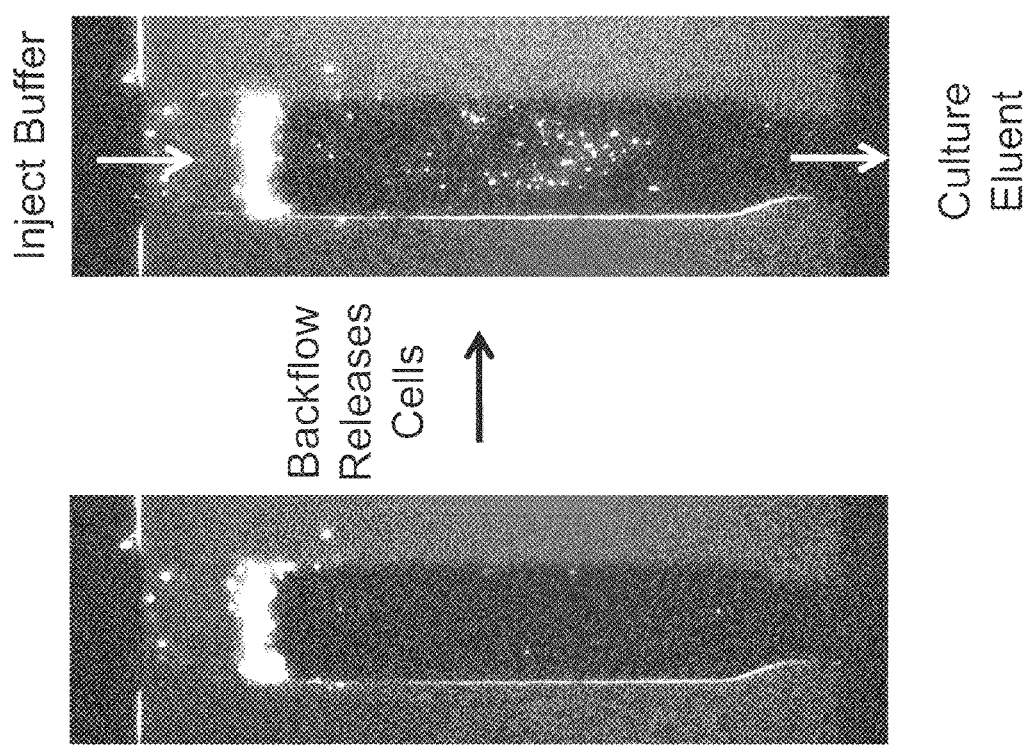
FIG. 14 show example fluorescence images of *E. coli* captured in an example of the disclosed device before and after applying a backflow.

To calculate the capture efficiency of the in-well filters, the captured bacteria was eluted and incubated off-chip on agar plates. To elute the bacteria, a buffer was injected while directing the fluid flow backwards through the filters. This was accomplished by blocking the outer-channel inlet and the inner-channel outlet, resulting in backflow of buffer from the outer-channel outlet, entering the wells via the well outlets and exiting via the well inlets, and finally exiting the example device from the inner-channel inlet. The backflow of buffer forces bacteria out of the filters back towards the inlet. The eluent was cultured overnight at 37° C. and the colonies were counted. FIG. 14 shows example fluorescence images of *E. coli* expressing green fluorescent protein (GFP) captured in the in-well filter before and after applying a backflow.

Effect of electrodeposition and surface fouling on the on-chip electrodes was also studied for the example device.

As described above with reference to FIG. 11, the working electrodes in each well were electroplated with $HAuCl_4$ to increase the electrode surface area. This was found to increase the magnitude of the acquired signal and thus, the detection sensitivity.

Figure 15:
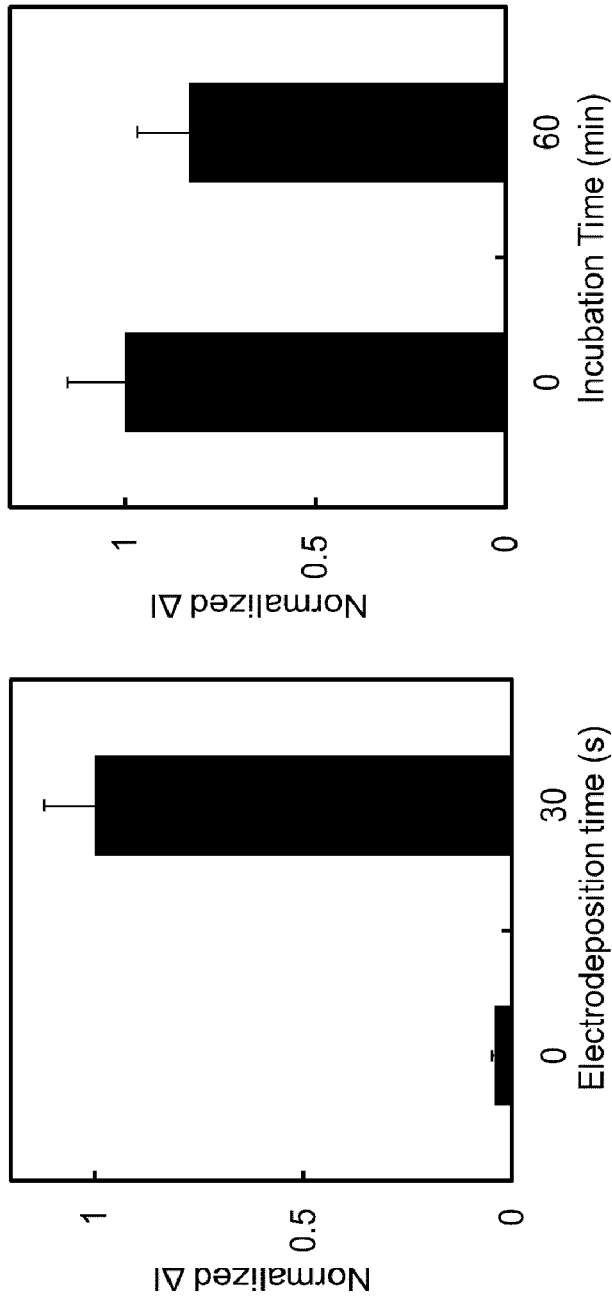
FIG. 15A shows results of electrochemical measurements of resazurin before and after electrodepositing on electrodes in an example of the disclosed device.
FIG. 15B illustrates the effect of surface fouling on the electrodes in an example of the disclosed device.

FIGS. 15A and 15B are charts illustrating the effect of electrodeposition and surface fouling on the on-chip electrodes. FIG. 15A shows results of electrochemical scans on-chip of 1 mM resazurin before and after electrodepositing Au for 30 s. Electrodeposition was found to increase the electrode surface area and thus the magnitude of the current. FIG. 15B illustrates the effect of surface fouling on the electrodes. After incubating for one hour, a slight signal decrease was observed when scanning on-chip with 1 mM resazurin. Currents are normalized to the maximum current.

An example study was carried out to determine bacterial capture efficiency. In this study, a 100 μL volume of serial dilutions of *E. coli* were introduced into the capture device at 10 μL/min. After capture, the device was washed with 100 μL of PBS buffer. Finally the bacteria were eluted in sterile PBS buffer. The eluted volume was plated on LB agar plates overnight at 37° C. and the colonies were counted.

Another example study was carried out to investigate electrochemical detection of bacteria using the example device. Serial dilutions of *E. coli* were spiked in buffer and introduced into the chip at 20 μL/min followed by 200 μL of 1 mM resazurin in LB broth. Air was flushed through the device to form the wells followed by FC-40, a fluorinated oil. The device was incubated in a water bath at 37° C.

An antibiotic susceptibility microdilution assay was also performed using the example device. Cultured *E. coli* were diluted to 100 cfu/μL and incubated at 37° C. in a 96 well plate in Nutrient Broth with serial dilutions of ciprofloxacin and ampicillin. After 24 hours, the absorbance at 600 nm was measured.

The performance of the example device for electrochemical detection in urine was investigated. Human urine (BioreclamationlVT) was centrifuged at 5000 g for 5 min to remove large particulates. *E. coli* and *K. pneumoniae* were diluted to 100 cfu/μL and spiked in the urine. Samples (200 μL) were introduced at 20 μL/min. Next, 200 μL of either ampicillin or ciprofloxacin in 1 mM resazurin and LB media were introduced at 20 μL/min. Air was flushed through the device to form the wells followed by FC-40 (200 μL) (Sigma Aldrich, St. Louis, Mo.). Thus the total volume of all solutions introduced is 600 μL which requires 30 min to process at 20 μL/min. The device was incubated in a water bath at 37° C. for 1 hour. 10 minutes were required to scan the leads. Thus the total time for the assay from sample introduction to readout was 1 hour and 40 minutes.

The performance of the example device was also investigated for electrochemical detection in unpurified urine. *E. coli* were diluted to 100 cfu/μL and spiked in the unpurified human urine (BioreclamationIVT). The spiked urine (200 μL) was passed through a 10 μm filter to remove large particulates and directly introduced at 20 μL/min into the chip. Next, 200 μL of either ampicillin or ciprofloxacin in 1 mM resazurin and LB media were introduced at 20 μL/min. Air was flushed through the device to form the wells followed by FC-40 (Sigma Aldrich, St. Louis, Mo.). The device was incubated in a water bath at 37° C.

One example study tested the limit of detection that could be achieved by monitoring the electrochemical signal of resazurin by incubating serial dilutions of *Escherichia coli* (*E. coli*) with 1 mM resazurin in LB culture media for 5 hours at 37° C.

Figure 2A:
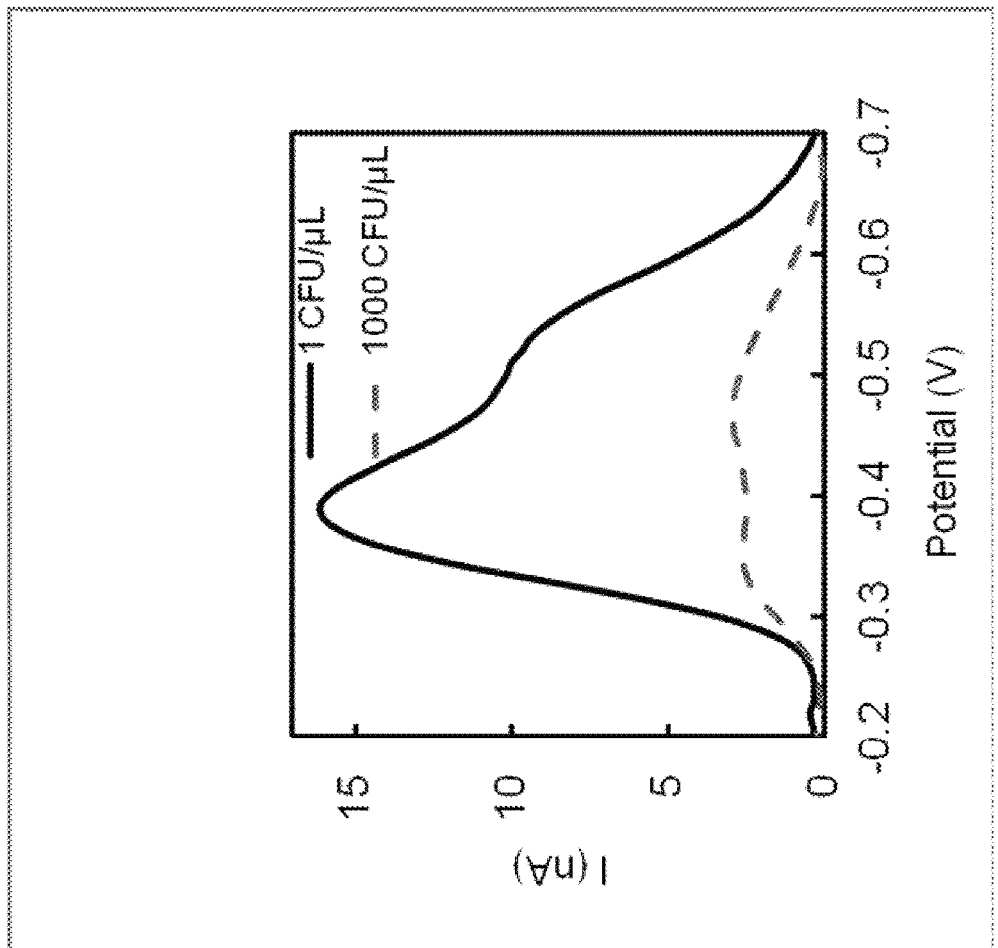
FIG. 2A shows representative differential pulse voltammograms obtained from culturing serial dilutions of E. coli for 5 hours with resazurin.

FIG. 2A shows representative DPVs obtained from culturing serial dilutions of *E. coli* for 5 hours with resazurin. DPVs of resazurin in LB media were found to exhibit two peaks. Peak I corresponds to the conversion of resazurin to resorufin through an irreversible 2-electron process, while peak II corresponds to the reversible reduction of resorufin to dihydroresorufin. Peak I was found to decrease systematically as metabolically active bacteria metabolize resazurin. Electrochemical scans were acquired with respect to the on-chip Au reference electrode which causes the peak current to shift to more negative potentials when compared to the Ag/AgCl reference electrode.

Figure 2B:
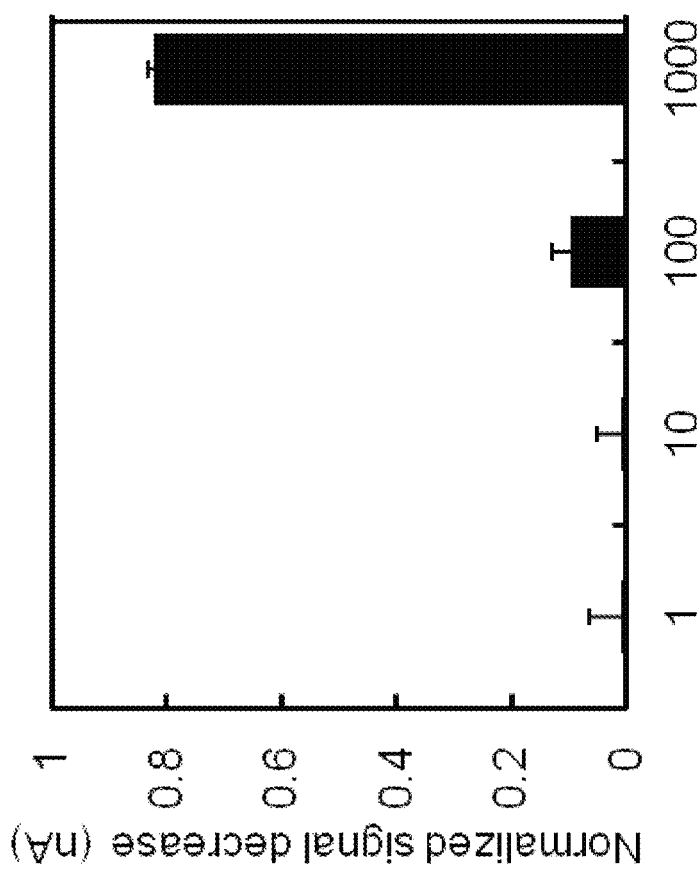
FIG. 2B shows the average signal decrease obtained after culturing E. coli for 5 hours with resazurin.
Figure 2C:
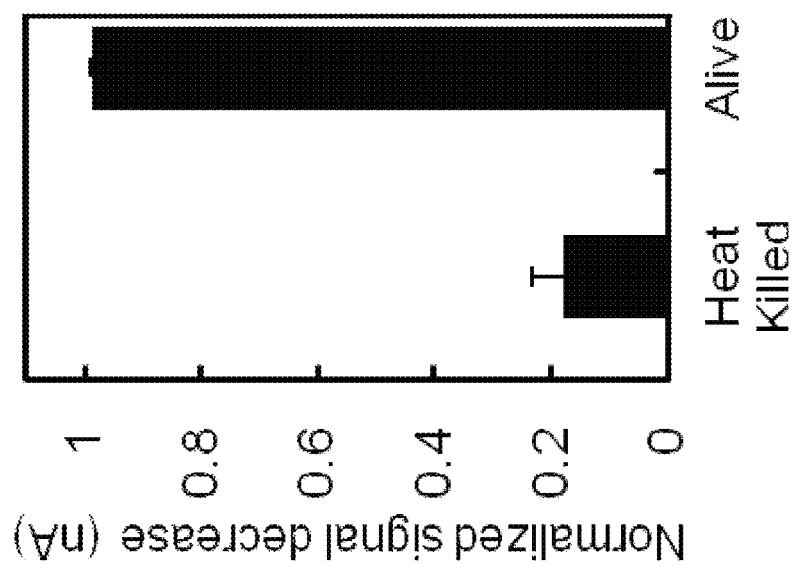
FIG. 2C shows the average signal decrease obtained when the metabolic activity of E. coli is stopped by heat death.

The average peak currents at −0.35 V as a function of bacterial concentration are plotted in FIG. 2B. FIG. 2B shows the average signal decrease obtained after culturing *E. coli* for 5 hours with resazurin. Data shown represents the average of at least 8 replicates. Error bars represent standard error. FIG. 2C shows the average signal decrease obtained when the metabolic activity of *E. coli* is stopped by heat death, indicating that metabolically inactive bacteria do not reduce resazurin.

In the example study, a detection limit of 100 CFU/μL was found, which may be clinically relevant and has been used as a threshold level for the presence of bacteriuria.[33,2] The peak signals was found to decrease with increasing bacterial concentration, as expected given that viable bacteria convert resazurin to resorufin. As there is significant overlap between peaks I and II, a decrease in the height of peak I causes peak II to decrease as well.

Figure 9:
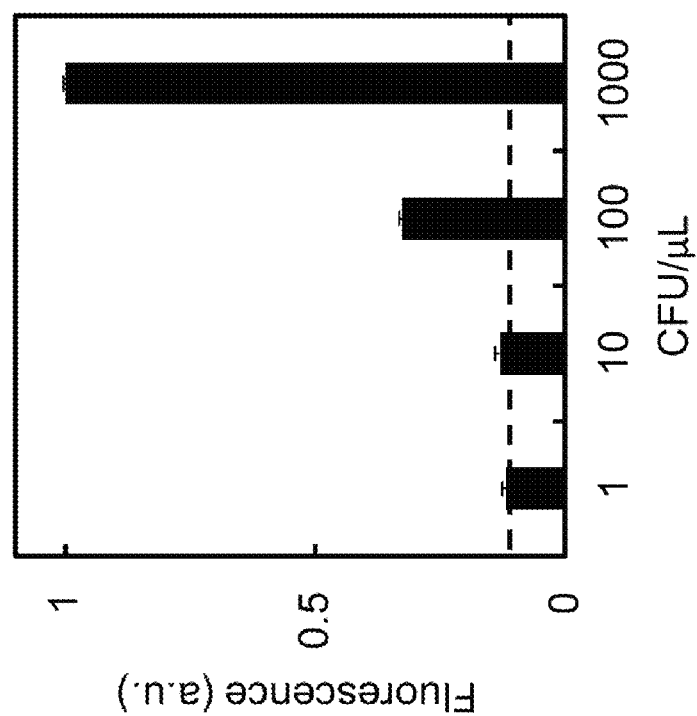
FIG. 9 shows example results from fluorescent detection of metabolically active *E. coli*.

The detection limit of electrochemical and fluorescent detection of bacterial viability using resazurin was also compared. This comparison found a similar limit of detection of 100 CFU/μL indicating that electrochemical detection of resazurin may be just as sensitive as fluorescent readout. FIG. 9 shows example results from fluorescent detection of metabolically active *E. coli*. Serial dilutions of *E. coli* were incubated for 5 hours at 37° C. with 1 mM resazurin in LB media. The fluorescence signal was measured using a microplate reader at 585 nm with an excitation wavelength of 570 nm. Metabolically active bacteria convert resazurin to resorufin which increases the fluorescence signal. 100 CFU/μL were detectable using fluorescence which corresponds with the detection limit achieved using electrochemistry using the same 5 hr incubation period. The dashed line represents the signal from the blank sample.

Compared to detection using fluorescence, using electrochemistry for detection may be more useful in that it typically does not require complicated or bulky instrumentation for readout and the sensors (e.g., electrodes) may be integrated directly into the culture chambers. In contrast, in the most sensitive fluorescence assays, the assay is typically performed in a series of nanoliter droplets which usually require a high-powered fluorescence microscope for sequential readout of the droplets. Using electrochemistry, it may be possible to integrate the sensors directly into the nanoliter culture chambers, eliminating the need for expensive optical equipment for readout. The electronics required for electrochemical readout may be integrated into a small benchtop or handheld device, which may help to lower the cost and/or footprint of the device.

Figure 3A:
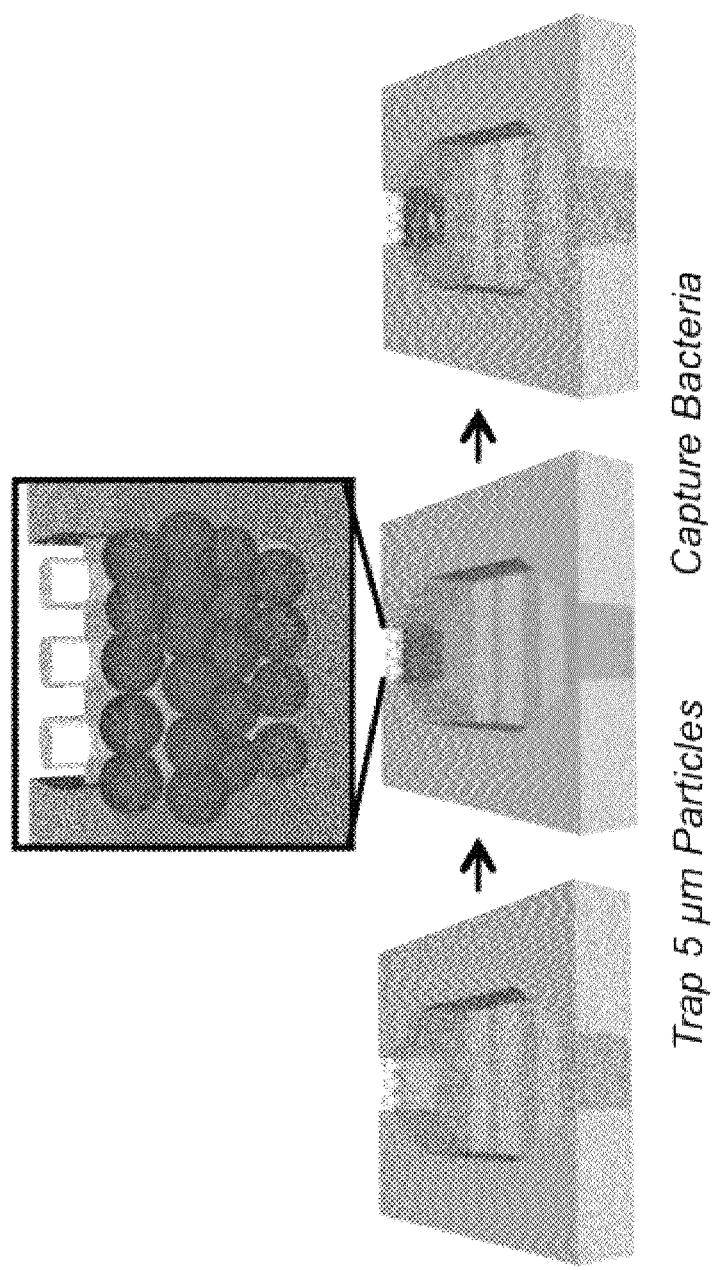
FIG. 3A is another schematic of in-well bacterial capture using an example of the disclosed device.
Figure 3B:
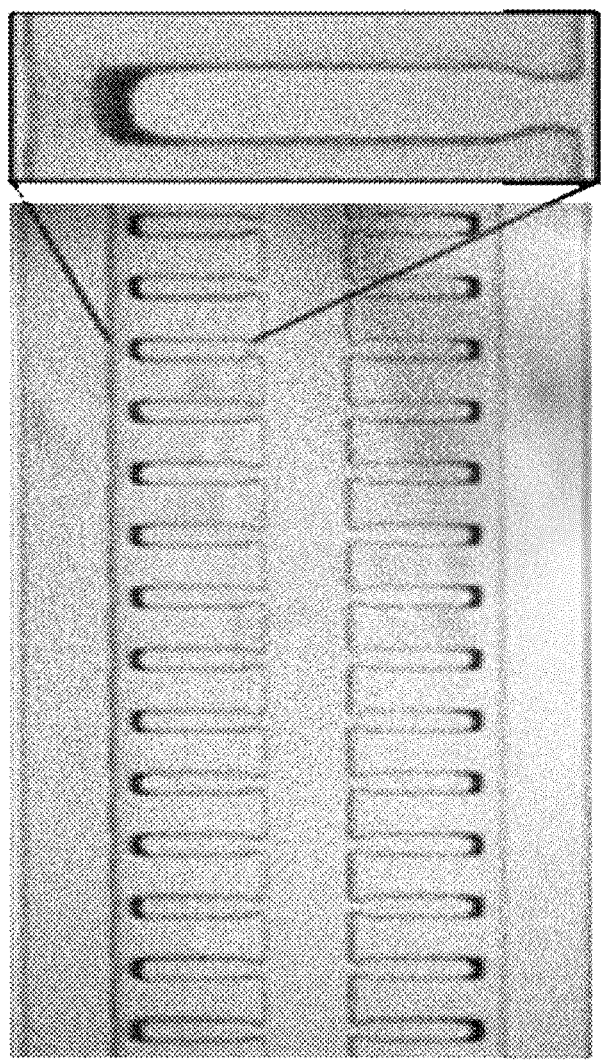
FIG. 3B is an example optical image of a microfilter of a well including microbeads.
Figure 3C:
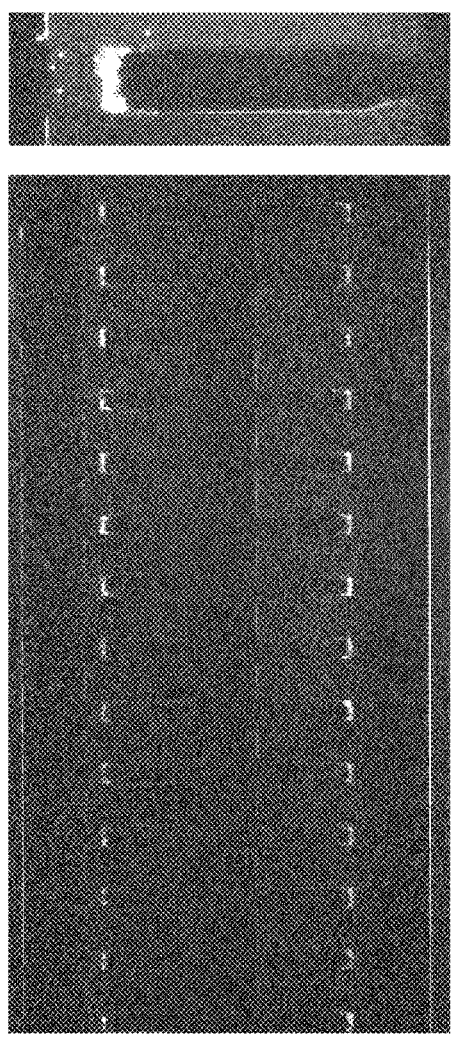
FIG. 3C is a fluorescence image showing *E. coli* trapped within the wells by the microbead filter.

Another study was carried out for validation of in-well bacterial capture using the example device. FIG. 3A is another schematic of in-well bacterial capture using the example device. Bacteria are trapped within in-well size-based filters fabricated from a bed of polystyrene beads immobilized within each well. FIG. 3B is an example optical image of a filter including microbeads immobilized at a pre-fabricated in-well barrier. FIG. 3C is a fluorescence image showing *E. coli* expressing GFP trapped within the wells by the microbead filter. These results indicated that bacteria were reproducibly captured within each well.

Figure 3D:
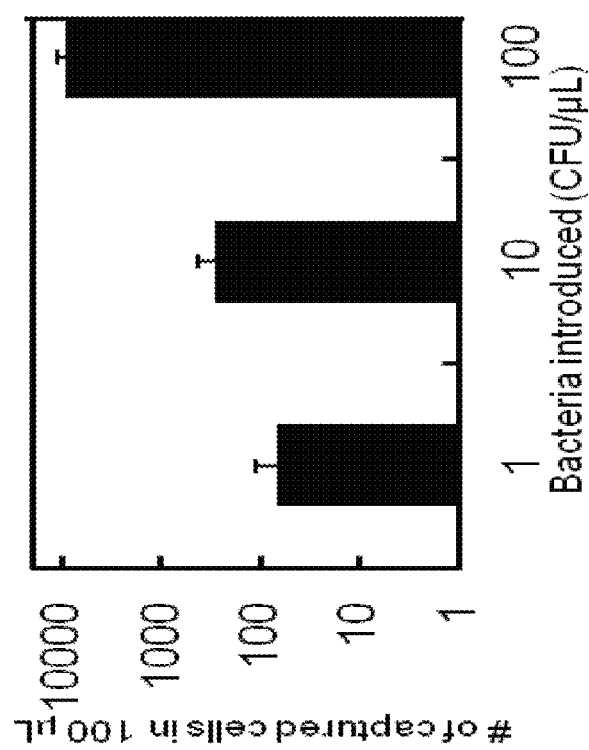
FIG. 3D shows the capture efficiency of an example of the disclosed device as a function of concentration of bacteria introduced.

To quantitate the capture efficiency of the example device, serial dilutions of a 100 μL volume of GFP *E. coli* were introduced at a flow rate of 10 μL/min. After capture, bacteria were introduced onto agar plates and the *E. coli* colonies were counted after incubating the plates overnight. FIG. 3D shows the capture efficiency as a function of concentration of bacteria introduced. These results suggest that the example device may achieve ~80% capture at concentrations as low as 1 cfu/μL.

With effective capture demonstrated by the example studies discussed above, other studies were carried out to test the ability of the disclosed device and method to detect viable bacteria captured within the wells. The example device was challenged with *E. coli* at 100 cfu/μL, a clinically relevant concentration in urinary tract infections.[2] This concentration corresponds to over 100 bacteria per well. The time dependence of the signal was studied to determine the minimum time necessary to detect a clinically relevant concentration of viable bacteria.

FIG. 4 is a chart illustrating in-well electrochemical measurement of bacterial viability. Electrochemical signal generated by resazurin was found to decrease as a function of incubation time for *E. coli* at 100 cfu/μL. Viable *E. coli* were detected within 30 minutes. For comparison, no positive signal change was observed after a 60 minute incubation in controls using a blank culture media and both purified and unpurified urine without spiked bacteria. These results represent a greater than 5-fold reduction in incubation time over the previous record of 2.8 hr.[20] A small signal increase was observed in the case of blank media which may be due to small chip-to-chip variations. Some signal decrease was observed in the case of blank urine and unpurified urine which could be attributed to surface fouling of the electrode as well. The signal decrease was calculated by subtracting the acquired peak current from the maximum peak current of 11 nA.

The above-discussed studies demonstrated the suitability of the disclosed device and method for detection of viable bacteria. Other studies were carried out to assess the suitability of the example device to rapidly determine the antibiotic resistance profile of bacteria in undiluted urine. To better simulate a clinical sample the study tested uropathogenic strains of *E. coli* (UPEC) and *Klebsiella pneumoniae* (*K. pneumoniae*), two of the most common pathogens implicated in urinary tract infections.[2] The *K. pneumoniae* strain was isolated from the urine of an infected patient and produces extended spectrum β-lactamase enzymes which confer resistance to a wide variety of β-lactam antibiotics.[2] In this study, susceptibility to two commonly used antibiotics to treat urinary tract infections—ampicillin, a β-lactam antibiotic; and ciprofloxacin, a fluoroquinolone—were tested.[35]

Figure 16:
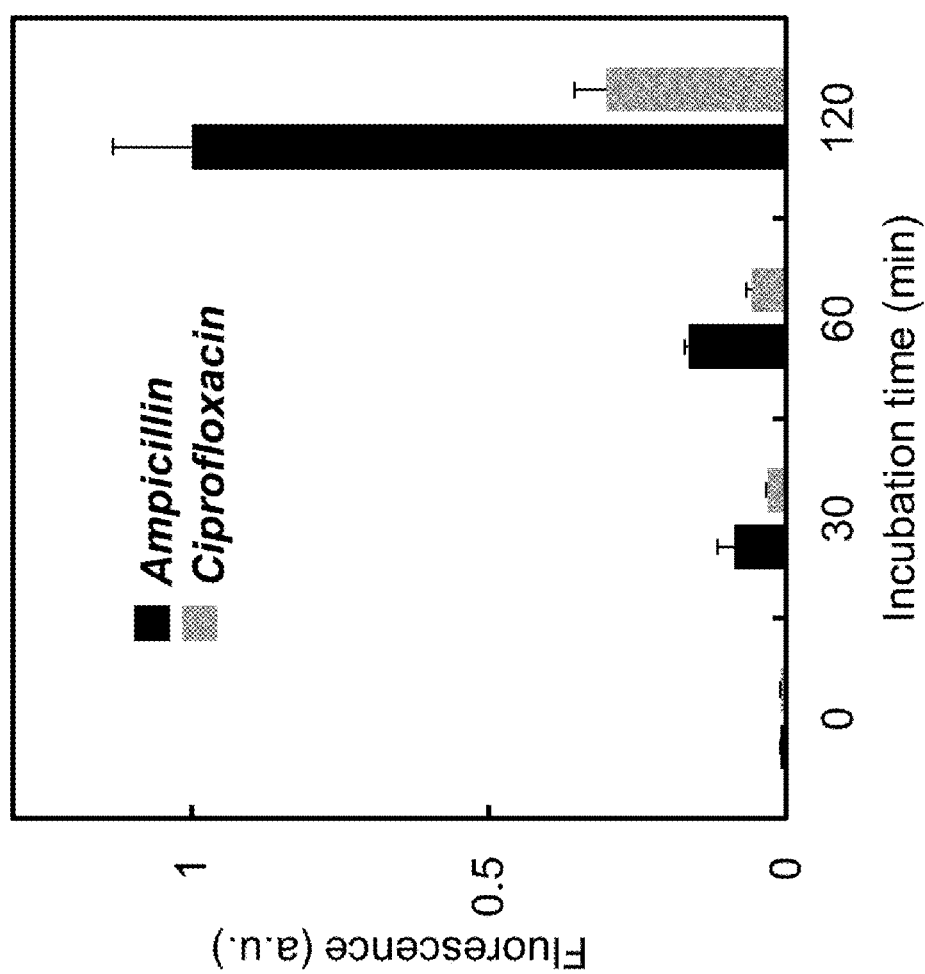
FIG. 16 shows example results indicating the time required for antibiotics to hinder the metabolic activity of bacteria.

In order to choose a suitable incubation period for the susceptibility test, the time required for the antibiotics to begin inhibiting bacterial metabolic activity was investigated. To study this, a high concentration of bacteria was used in order to determine the minimum time required for the bacteria to exhibit differential metabolic activity in response to the tested antibiotics. *K. pneumoniae* at $1\times10^5$ cfu/µL were incubated at 37° C. in the presence of ampicillin and ciprofloxacin at 100 µg/mL in LB media and 1 mM resazurin. The increase in fluorescence induced by the conversion of resazurin by metabolically active bacteria was recorded. FIG. 16 shows example results indicating the time required for antibiotics to hinder the metabolic activity of bacteria. The signal from the sample incubated with ciprofloxacin was found to be suppressed within 30 minutes, indicating that the antibiotic rapidly inhibits the metabolism of *K. pneumoniae*. As this strain of *K. pneumoniae* is resistant to ampicillin, the fluorescence increases as *K. pneumoniae* convert resazurin. These results indicate that the chosen incubation period of 60 minutes for the susceptibility test is sufficiently long for the bacteria to exhibit differential metabolic activity in response to the tested antibiotics.

As discussed above, the effect of surface fouling induced by incubating the devices with LB media was also studied, with example results shown in FIG. 15B. The results indicate only a small change in the acquired signals before and after incubation, indicating that fouling could be attributed to approximately a 15% signal change which may be acceptable in cases where the example device is not intended for reuse.

Figure 5A:
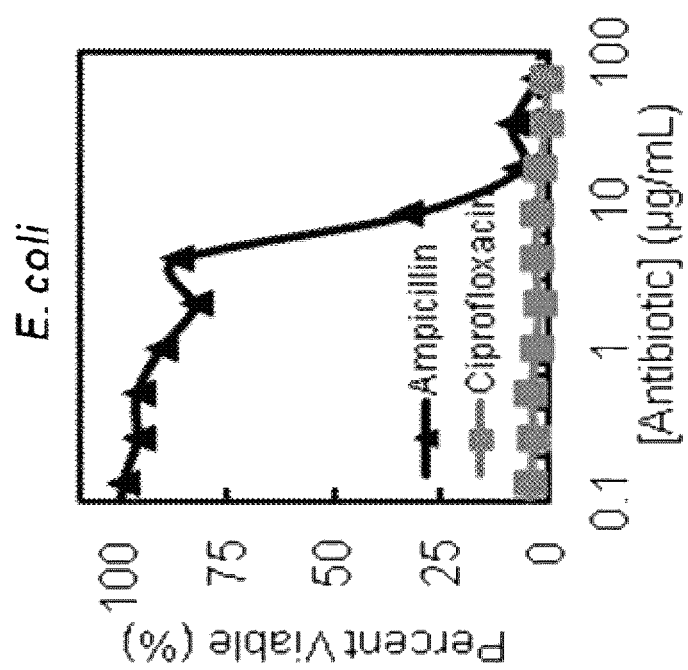
FIGS. 5A-5E are charts illustrating the susceptibility of *E. coli* and *K. pneumoniae* to ampicillin and ciprofloxacin.
Figure 5B:
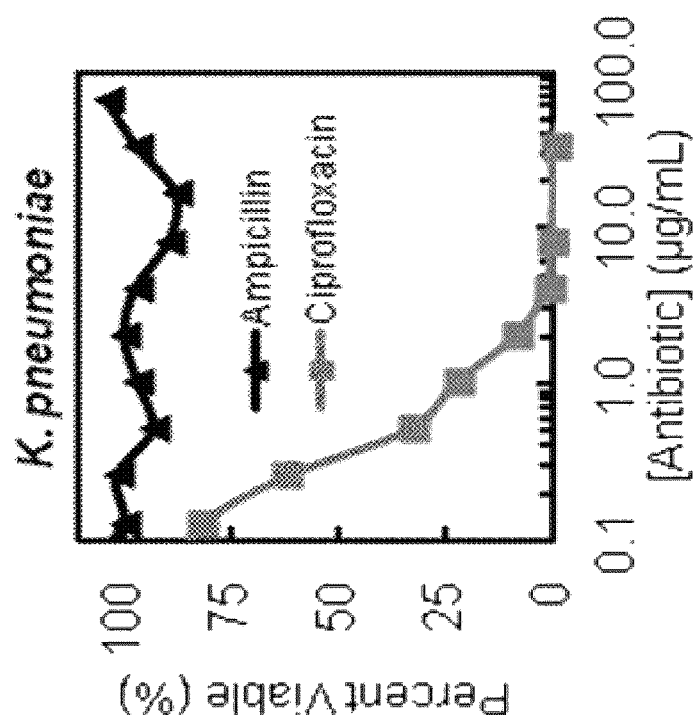
Figure 5C:
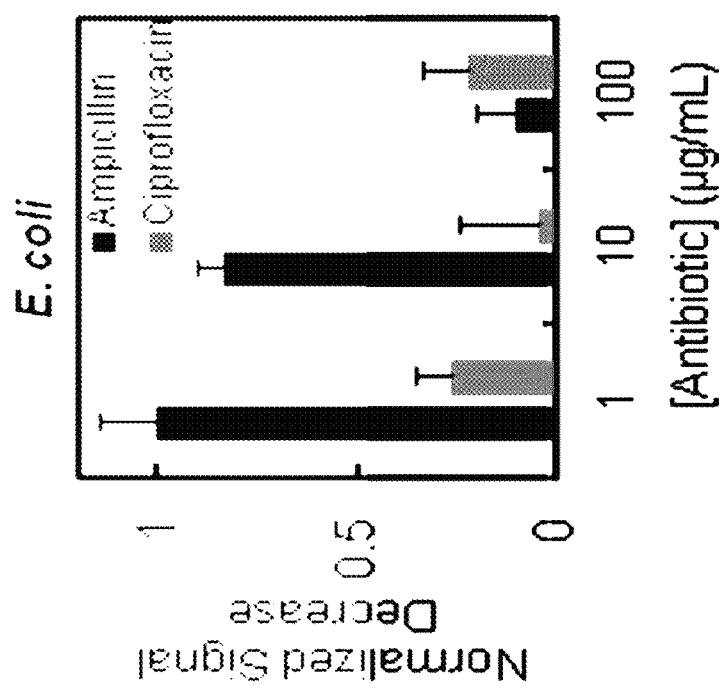
Figure 5D:
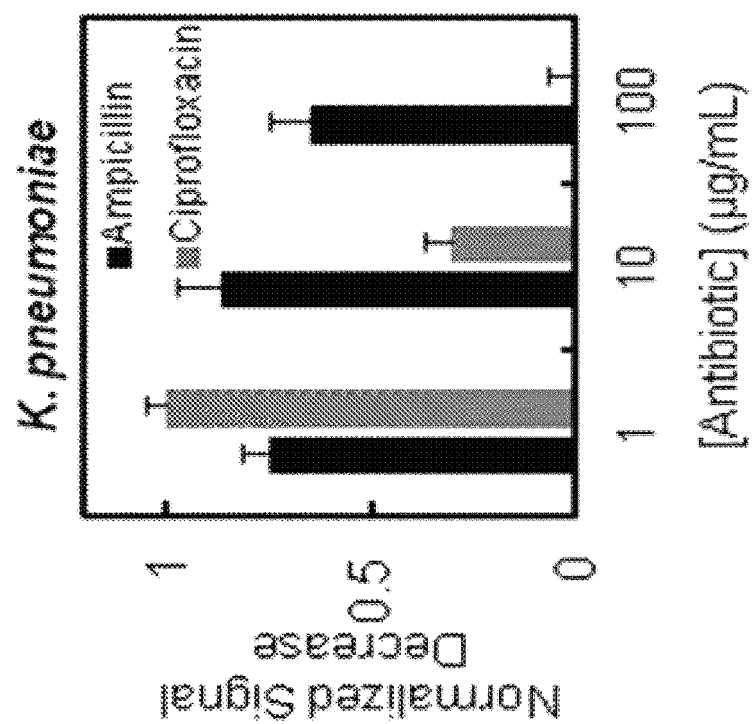

*E. coli* (UPEC) and *K. pneumoniae* present at 100 cfu/µL in undiluted urine were introduced into the example device. After capture, a culture medium, resazurin, and either ampicillin or ciprofloxacin were introduced. FIGS. 5C and 5D show the electrochemical signal obtained as a function of antibiotic concentration after a 1 hour incubation at 37° C. No signal change was observed with a blank sample of urine.

For the *E. coli* strain, the signal was found to be low for all ciprofloxacin concentrations, indicating the bacteria are susceptible to the antibiotic at concentrations above 1 µg/mL (see FIG. 5C). The signal was found to decrease with ampicillin concentration indicating susceptibility at concentrations between 10 and 100 µg/mL. These results were confirmed using a standard microdilution assay with a 24 hour incubation, to determine the antibiotic resistance profile of *E. coli* and *K. pneumoniae* to ampicillin and ciprofloxacin (FIGS. 5A and 5B). The minimum antibiotic concentration that inhibits 90% of *E. coli* bacterial growth ($MIC_{90}$) was found to be 16 µg/mL for ampicillin and less than 0.1 µg/mL for ciprofloxacin. For *K. pneumoniae*, the signal was found to be approximately constant with increasing ampicillin concentration, indicating that bacterial viability is not affected by the ampicillin dose—the hallmark of resistance. As this strain produces a beta lactamase, resistance to ampicillin, a beta-lactam antibiotic is expected. In contrast, a concentration-dependent signal was observed with ciprofloxacin, indicating that bacterial viability is reduced by increasing ciprofloxacin concentration. This indicates that this strain is susceptible to ciprofloxacin and was found to be inhibited at concentrations between 1 and 10 µg/mL (see FIG. 5D). Using a standard microdilution assay, the *K. pneumoniae* were indeed found to be resistant to ampicillin but susceptible to ciprofloxacin (see FIG. 5B). The $MIC_{90}$ of *K. pneumoniae* was found to be 2 µg/mL for ciprofloxacin and greater than 100 µg/mL for ampicillin.

Figure 17:
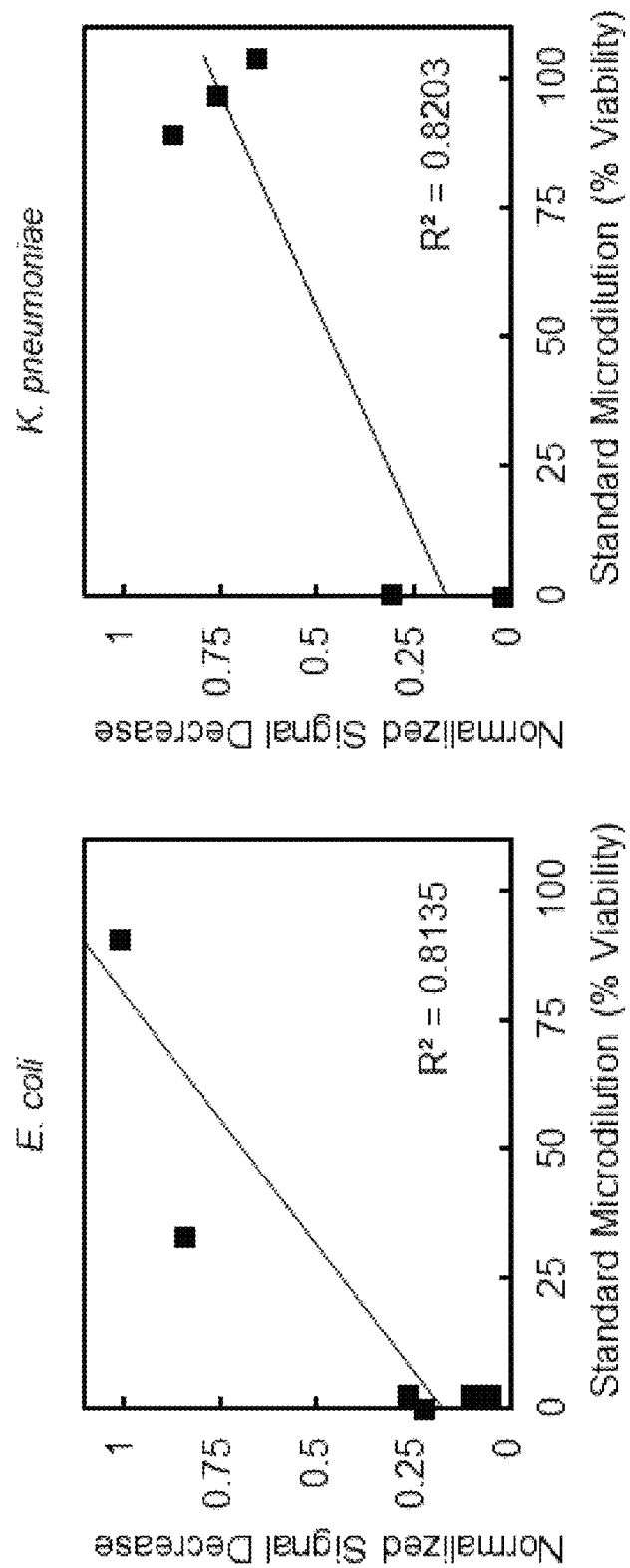
FIG. 17 illustrates the correlation between susceptibility assays performed using an example of the disclosed device and conventional assays.

For both strains, these results obtained using the example device show good agreement with the MIC determined using the gold standard method which required incubation times over 20 times longer than the on-chip assay using the example device. Good correlation was found between the on-chip susceptibility assay and standard assays with $r^2$ values of 0.81 and 0.82 for *E. coli* and *K. pneumoniae* respectively (see FIG. 17). Slight discrepancy may be attributable to the different detection methodologies and incubation periods used when comparing the two methods.

Figure 5E:
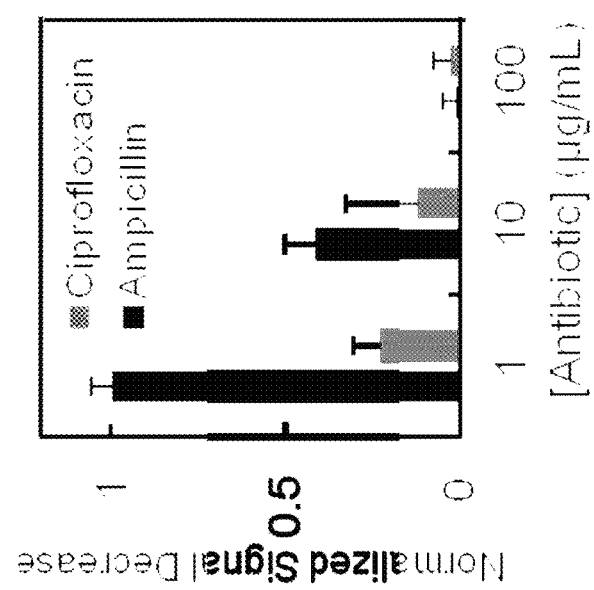

A series of experiments were also performed to determine the antibiotic susceptibility of bacteria in unpurified urine. FIG. 5E shows examples results from electrochemical determination, using the example device, of the antibiotic susceptibility of *E. coli* in unpurified urine after incubating with different levels of antibiotic at 37° C. for 1 hour. Currents are normalized to the maximum value. Error bars represent standard error.

Figure 18:
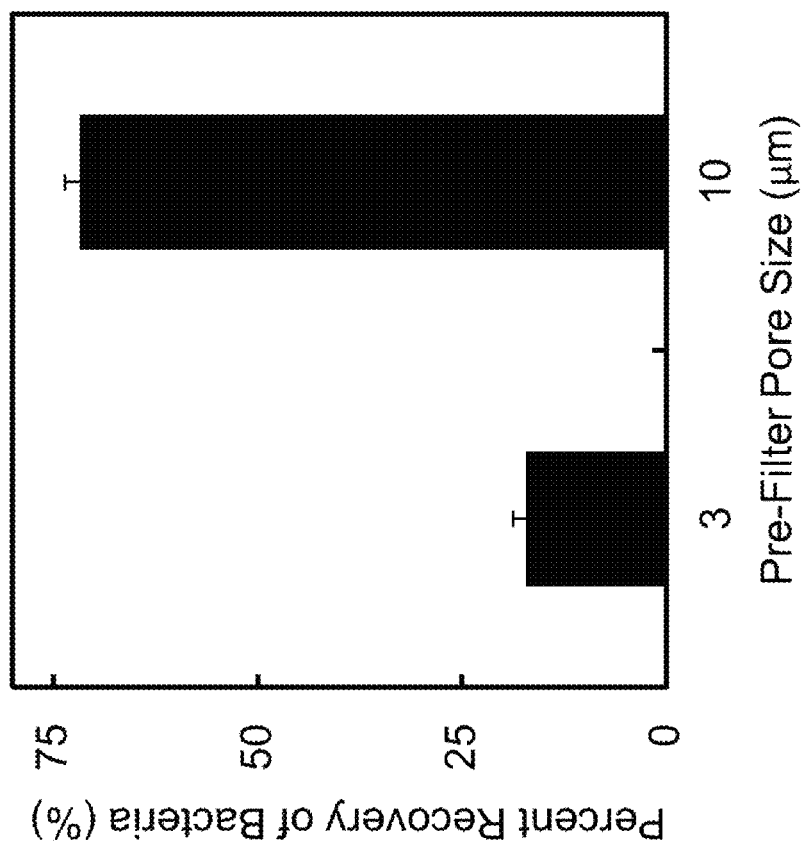
FIG. 18 illustrates the effect of pre-filter size on recovery of bacteria spiked in undiluted urine.

*E. coli* were spiked directly into undiluted and unpurified urine at 100 cfu/µL. The sample was passed through a 10 µm filter that removed large particulates while allowing bacteria to pass. FIG. 18 illustrates the effect of pre-filter size on recovery of bacteria spiked in undiluted urine. *E. coli* was found to be efficiently recovered directly from urine using a pre-filter with a 10 µm pore diameter. The filtrate was introduced into the example device and tested against ampicillin and ciprofloxacin by incubating at 37° C. for 1 hour. It was found that the *E. coli* were susceptible to ciprofloxacin at concentrations 1 µg/mL and above and susceptible to ampicillin at a concentration between 10 and 100 µg/mL. No appreciable signal change was found when using a blank control sample of unpurified urine (see FIG. 4, discussed above). These results were found to agree with the standard microdilution antibiotic susceptibility assay indicating that the device can be challenged with unpurified urine samples using a simple inline pre-filtration sample processing step.

Representative electrochemical scans acquired using the example device are shown in FIGS. 19A-19D. These charts show example electrochemical scans acquired on-chip after introducing *E. coli* spiked in urine at 100 CFU/µL and subsequently introducing 1 mM resazurin and an antibiotic. Samples were incubated for 60 min at 37° C. *E. coli* were incubated with 100 µg/mL ampicillin (FIG. 19A), 1 µg/mL ampicillin (FIG. 19B), 100 µg/mL ciprofloxacin (FIG. 19C), and 1 µg/mL ciprofloxacin (FIG. 19D). In the presence of 1 µg/mL ampicillin, the magnitude of the signal was found to be reduced as that concentration of ampicillin is insufficient to inhibit the metabolism of *E. coli*. Electrochemical scans were acquired on-chip with the Au reference electrode of the example device. Peaks are shifted to more negative potentials when compared to using the Ag/AgCl reference electrode.

To test undiluted urine on chip, large particulates were removed from urine while allowing bacteria to pass through the filter. Various pre-filter sizes were tested to ensure that bacteria spiked in whole urine could be recovered. *E. coli* were spiked at $1\times10^2$ cfu/µL into whole urine and 100 µL of the urine was passed through the pre-filters with various pore diameters. The filtrate was plated on agar plates and incubated overnight at 37° C. The number of bacterial colonies was counted and it was found that using a 10 µm pre-filter, nearly 75% of bacteria could be recovered directly from whole urine.

In various examples, the present disclosure describes methods and devices that may offer faster reported detection of antibiotic susceptibility at clinically relevant concentrations directly from unpurified urine, compared to conventional approaches. The rapid turnaround time may be facilitated by concentrating the bacteria in a nanoliter volume which increases the local effective concentration of bacteria. The turnaround time may be further reduced by incubating the bacteria in isolated nanoliter compartments which allows the reduced form of resazurin to rapidly accumulate to detectable levels by confining diffusion. The disclosed approach is also purely electronic, which may facilitate the development of antibiotic susceptibility tests at the point-of-care by reducing or eliminating the need for expensive and bulky optical equipment.

In a clinical setting, an example of the disclosed device could serve as an alternative to standard susceptibility tests to provide results, for example with a 1 hour incubation, after initial culture-based identification of the bacteria. Currently, conventional antibiotic susceptibility tests typically require an additional 18-24 hours after the initial culture step.

Examples of the disclosed device could also be used in conjunction with standard culture-based antibiotic susceptibility tests to provide point-of-care susceptibility results directly from undiluted urine with a 1 hour incubation period. This may permit the rapid administration of an effective antibiotic in the interim until the results of standard antibiotic susceptibility tests are available 2-3 days later, at which point the therapy could be refined. This may allow doctors to administer a targeted antibiotic almost immediately, which may improve patient outcomes and may curb the rise of antibiotic resistance by decreasing the use of broad spectrum antibiotics. In infections which lead to urosepsis, the most severe UTIs, the disclosed method and device may have clinical utility as these infections typically require immediate administration of effective antibiotics.[4]

In example studies discussed above, it was found that, when challenged with a sample containing a single bacterial strain, the example disclosed device accurately and rapidly determined the susceptibility to various antibiotics. To enable accurate detection in the case of multiple infecting species (although polymicrobial infections are not common (5%-11%) in urosepsis[36]), the multiple nanoliter chambers of the example device may be devoted to multiplexed combinations of bacteria combined with local metabolic sensing.

Using an electrochemical approach capable of detecting metabolically active bacteria, the example disclosed method and device was able to achieve the detection of live bacteria using a relatively short 30 minute incubation period. By concentrating and analysing the bacteria within miniaturized compartments in the example device, the time required to detect viable bacteria may be reduced. The assay disclosed herein may be used to monitor bacterial metabolism in response to antibiotics to rapidly readout the antibiotic susceptibility profile. This approach may allow for rapid administration of antibiotics before the results of standard culture-based susceptibility testing are available.

The present disclosure describes examples for detecting the metabolic activity of bacteria, to test susceptibility to antibiotics. However, the present disclosure may also be suitable for detecting the metabolic activity of other target cells. For example, the present disclosure may be used, with modifications as appropriate, for detecting mammalian cells (e.g., cancer cells), fungus (e.g., yeast), and may be used to test for their susceptibility to compounds designed to inhibit their activity. For example, a similar resazurin-based assay may be used to detect metabolic activity of mammalian cells, or fungus. Other reporter compounds, such as methylene blue, formazan or tetrazolium salts, may also be used. The sample may also be other than a buffer or a urine sample; for example, the sample may be any suitable biological or non-biological sample, including biological samples such as a blood sample (which may be pre-treated as appropriate to avoid clogging the microfilters in the example device), a sputum sample, a plasma sample, or other tissue sample, or non-biological samples such as a water sample (e.g., for testing bacteria levels in a water supply) or a buffer sample. Pre-processing may be carried out as appropriate to isolate cells of interest from these samples.

Since the disclosed device and method may provide measurements representing metabolic activity of target cells in each well, the disclosed device and method may be used as a measurement of the relative amount of metabolically active target cells in a sample, compared to a control, for example.

Examples of the present disclosure may be useful for estimating a mean number of cells in a sample, since the change in detectable electrochemical signal may be dependent (e.g., proportional) to the number of cells that affect the reporting compound. To improve such an estimate, measurements from a plurality of wells may be averaged together; additionally or alternatively, a well may have a plurality of electrodes to obtain multiple measurements from the same well, which may all be averaged together. The measurement may be compared against a lookup-table or reference chart that indicates the expected measurement for a known concentration of cells, for example.

Examples of the present disclosure may be used to determine the minimum inhibitory concentration (MIC) of a given antibiotic against a given microorganism. As part of an antimicrobial susceptibility testing (AST) report, the MIC value may be included to guide prescription, for example.

The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entirety.

REFERENCES

1. S. B. Levy and B. Marshall, *Nat. Med.,* 2004, 10, S122-9.
2. B. Foxman, *Nat. Rev. Urol.,* 2010, 7, 653-60.

3. M. A. Pfaller and R. N. Jones, *Arch. Pathol. Lab. Med.*, 2006, 130, 767-778.
4. F. M. E. Wagenlehner, A. Pilatz, and W. Weidner, *Int. J. Antimicrob. Agents*, 2011, 38, 51-57.
5. W. J. McIsaac and C. L. Hunchak, *Med. Decis. Making*, 2011, 31, 405-11.
6. V. Perreten, L. Vorlet-fawer, P. Slickers, R. Ehricht, P. Kuhnert, and J. Frey, *J. Clin. Microbiol.*, 2005, 43, 2291.
7. B. Strommenger, C. Kettlitz, G. Werner, and W. Witte, *J. Clin. Microbiol.*, 2003, 41, 4089.
8. S. Shenai, F. Krapp, J. Allen, R. Tahirli, R. Blakemore, R. Rustomjee, A. Milovic, M. Jones, S. M. O. Brien, D. H. Persing, S. Ruesch-gerdes, E. Gotuzzo, C. Rodrigues, D. Alland, and M. D. Perkins, *N. Engl. J. Med.*, 2010, 363, 1005-1015.
9. K. E. Mach, R. Mohan, E. J. Baron, M.-C. Shih, V. Gau, P. K. Wong, and J. C. Liao, *J. Urol.*, 2011, 185, 148-53.
10. M. C. Roberts, S. Schwarz, and H. J. M. Aarts, Front. *Microbiol.*, 2012, 3, 384.
11. G. Longo, L. Alonso-Sarduy, L. M. Rio, A. Bizzini, A. Trampuz, J. Notz, G. Dietler, and S. Kasas, *Nat. Nanotechnol.*, 2013, 8, 522-6.
12. T. S. Mann and S. R. Mikkelsen, *Anal. Chem.*, 2008, 80, 843-8.
13. Y. Lu, J. Gao, D. D. Zhang, V. Gau, J. C. Liao, and P. K. Wong, *Anal. Chem.*, 2013, 85, 3971-6.
14. P. Ertl, B. Unterladstaetter, K. Bayer, and S. R. Mikkelsen, *Anal. Chem.*, 2000, 72, 4949-4956.
15. P. Ertl, M. Wagner, E. Corton, and S. R. Mikkelsen, *Biosens. Bioelectron.*, 2003, 18, 907-916.
16. K. Chotinantakul, W. Suginta, and A. Schulte, *Anal. Chem.*, 2014, 86, 10315-10322.
17. B. Li, Y. Qiu, A. Glidle, D. McIlvenna, Q. Luo, J. Cooper, H.-C. Shi, and H. Yin, *Anal. Chem.*, 2014, 86, 3131-3137.
18. M. W. Kadlec, D. You, J. C. Liao, and P. K. Wong, *J. Lab. Autom.*, 2013, 19, 258-266.
19. J. Palomino, A. Martin, M. Camacho, H. Guerra, J. Swings, and F. Portaels, *Antimicrob. Agents Chemother.*, 2002, 42, 2720-2722.
20. J. Q. Boedicker, L. Li, T. R. Kline, and R. F. Ismagilov, *Lab Chip.*, 2008, 8, 1265-72.
21. K. Churski, T. S. Kaminski, S. Jakiela, W. Kamysz, W. Baranska-Rybak, D. B. Weibel, and P. Garstecki, *Lab Chip.*, 2012, 12, 1629-37.
22. F. Deiss, M. E. Funes-Huacca, J. Bal, K. F. Tjhung, and R. Derda, *Lab Chip.*, 2014, 14, 167-71.
23. N. J. Cira, J. Y. Ho, M. E. Dueck, and D. B. Weibel, *Lab Chip.*, 2012, 12, 1052-9.
24. C. H. Chen, Y. Lu, M. L. Y. Sin, K. E. Mach, D. D. Zhang, V. Gau, J. C. Liao, and P. K. Wong, *Anal. Chem.*, 2010, 82, 1012-9.
25. D.-K. Kang, M. M. Ali, K. Zhang, S. S. Huang, E. Peterson, M. a. Digman, E. Gratton, and W. Zhao, *Nat. Commun.*, 2014, 5, 5427.
26. M. Safavieh, M. U. Ahmed, M. Tolba, and M. Zourob, *Biosens. Bioelectron.*, 2012, 31, 523-8.
27. M. Varshney, Y. Li, B. Srinivasan, and S. Tung, *Sensors Actuators B Chem.*, 2007, 128, 99-107.
28. K. Hsieh, A. S. Patterson, B. S. Ferguson, K. W. Plaxco, and H. T. Soh, *Angew. Chem. Int. Ed.*, 2012, 51, 4896-900.
29. A. S. Patterson, K. Hsieh, H. T. Soh, and K. W. Plaxco, *Trends Biotechnol.*, 2013, 31, 704-12.
30. L. Soleymani, Z. Fang, B. Lam, X. Bin, E. Vasilyeva, A. Ross, E. H. Sargent, and S. O. Kelley, *ACS Nano.*, 2011, 5, 3360.
31. S. Çakir and E. Y. Arslan, *Chem. Pap.*, 2010, 64, 386-394.
32. S. Khazalpour and D. Nematollahi, *RSC Adv.*, 2014, 4, 8431.
33. J. W. Warren, E. Abrutyn, J. R. Hebei, J. R. Johnson, A. J. Schaeffer, and W. E. Stamm, *Clin. Infect. Dis.*, 1998, 29, 745-758.
34. N. Bao, B. Jagadeesan, A. K. Bhunia, Y. Yao, and C. Lu, *J. Chrom. A.*, 2008, 1181, 153-8.
35. K. Gupta, T. M. Hooton, K. G. Naber, B. Wullt, R. Colgan, L. G. Miller, G. J. Moran, L. E. Nicolle, R. Raz, A. J. Schaeffer, and D. E. Soper, *J. Clin. Infect. Dis.*, 2011, 52, e103-20.
36. O. Braissant, G. Müller, A. Egli, A. Widmer, R. Frei, A. Halla, D. Wirz, T. C. Gasser, A. Bachmann, F. Wagenlehner, and G. Bonkat, *J. Clin. Microbiol.*, 2014, 52, 624-6.
37. R. Greenwood, P. F. Luckham, and T. Gregory, *J. Colloid Interface Sci.*, 1997, 191, 11-21.

The invention claimed is:

1. A device for detecting metabolic activity of target cells in a sample comprising a fluid solution, the device comprising:
   a plurality of individual nanoliter wells, each well being aligned along a respective longitudinal axis comprising:
   an inlet for receiving the sample at a first longitudinal end of the well;
   an outlet permitting exiting of the fluid solution from a second longitudinal end of the well opposite to the first longitudinal end;
   a microfilter positioned near the outlet for inhibiting the target cells from exiting the well through the outlet; and
   electrodes in the well for sensing an electrochemical state of contents in the well;
   a first channel perpendicular with the longitudinal axis of each well, the first channel being in fluid communication with all the inlets of the wells; and
   a second channel, separate from the first channel, perpendicular with the longitudinal axis of each well, the second channel being in fluid communication with all the outlets of the wells;
   wherein the first and second channels are each configured to enable introduction of a sealing fluid across all the inlets and all the outlets, respectively, to seal each well.

2. The device of claim 1, further comprising:
   controllable valves for sealing the inlet and outlet of the well.

3. The device of claim 1, wherein the microfilter comprises an assembly of microbeads.

4. The device of claim 3, wherein the microbeads are of different sizes.

5. The device of claim 1, wherein the microfilter comprises a microporous membrane.

6. The device of claim 1, wherein the electrodes in the well comprise a working electrode and a counter electrode.

7. The device of claim 6, wherein the electrodes in the well further comprise a reference electrode.

8. The device of claim 6, wherein a single well comprises a plurality of working electrodes.

9. The device of claim 1, wherein the device is disposable.

10. The device of claim 1, wherein the first channel is configured to flow the sealing fluid perpendicularly across all the inlets, to enable sealing of all the inlets of all the wells, and wherein the second channel is configured to flow the sealing fluid perpendicularly across all the outlets, to enable sealing of all the outlets of all the wells.

* * * * *